US011123040B2

(12) United States Patent
Mahfouz et al.

(10) Patent No.: US 11,123,040 B2
(45) Date of Patent: *Sep. 21, 2021

(54) REAL-TIME 3-D ULTRASOUND RECONSTRUCTION OF KNEE AND ITS IMPLICATIONS FOR PATIENT SPECIFIC IMPLANTS AND 3-D JOINT INJECTIONS

(71) Applicant: JointVue, LLC, Knoxville, TN (US)

(72) Inventors: Mohamed R. Mahfouz, Knoxville, TN (US); Ray C. Wasielewski, New Albany, OH (US)

(73) Assignee: JointVue, LLC, Knoxville, TN (US)

( * ) Notice: Subject to any disclaimer, the term of this patent is extended or adjusted under 35 U.S.C. 154(b) by 1040 days.

This patent is subject to a terminal disclaimer.

(21) Appl. No.: 15/627,346

(22) Filed: Jun. 19, 2017

(65) Prior Publication Data

US 2017/0281122 A1 Oct. 5, 2017

Related U.S. Application Data

(63) Continuation of application No. 14/250,957, filed on Apr. 11, 2014, which is a continuation of application No. PCT/US2012/060261, filed on Oct. 15, 2012.

(Continued)

(51) Int. Cl.
*A61B 8/14* (2006.01)
*A61B 8/00* (2006.01)
(Continued)

(52) U.S. Cl.
CPC .............. *A61B 8/0875* (2013.01); *A61B 8/14* (2013.01); *A61B 8/5207* (2013.01);
(Continued)

(58) Field of Classification Search
CPC ...................................................... G06T 7/564
See application file for complete search history.

(56) References Cited

U.S. PATENT DOCUMENTS 3,881,164 A 4/1975 Kossoff
4,476,873 A 10/1984 Sorenson et al.
(Continued)

FOREIGN PATENT DOCUMENTS

WO 2000063719 10/2000
WO 2010088696 3/2010
(Continued)

OTHER PUBLICATIONS

Mohamed R. Mahfouz. Operating Room of the Future Orthopedic Perspective. Biomedical Engineering Conference Dec. 18, 2008.
(Continued)

*Primary Examiner* — Luther Behringer
(74) *Attorney, Agent, or Firm* — Dorton & Willis LLP; Ryan Willis

(57) ABSTRACT

Methods and apparatus for treating a patient. The method includes acquiring a plurality of radio frequency (RF) signals with an ultrasound transducer, each RF signal representing one or more return echoes from a scan line of a pulse-mode echo ultrasound scan. A position of the ultrasound transducer corresponding to each of the acquired RF signals is determined, and a plurality of contour lines generated from the plurality of RF signals. The method estimates a 3-D shape and position of an anatomical feature, such as a joint of patient based on the generated contour lines and corresponding ultrasound transducer positions. An apparatus, or computer includes a processor and a memory with instructions that, when executed by the processor, perform the aforementioned method.

20 Claims, 17 Drawing Sheets

Related U.S. Application Data

(60) Provisional application No. 61/547,508, filed on Oct. 14, 2011.

(51) Int. Cl.
*A61B 8/08* (2006.01)
*G06T 7/564* (2017.01)
*G06T 17/00* (2006.01)

(52) U.S. Cl.
CPC ............ *A61B 8/5223* (2013.01); *G06T 7/564* (2017.01); *G06T 17/00* (2013.01); *A61B 8/4245* (2013.01); *G06T 2207/10028* (2013.01); *G06T 2207/10136* (2013.01); *G06T 2207/30008* (2013.01); *G06T 2210/41* (2013.01)

(56) References Cited

U.S. PATENT DOCUMENTS

| | | | |
|---|---|---|---|
| 5,394,875 | A | 3/1995 | Lewis et al. |
| 5,413,116 | A | 5/1995 | Radke et al. |
| 5,447,154 | A | 9/1995 | Cinquin et al. |
| 5,488,952 | A | 2/1996 | Schoolman |
| 5,771,310 | A | 3/1998 | Vannah |
| 5,806,521 | A | 9/1998 | Morimoto et al. |
| 6,106,464 | A | 8/2000 | Bass et al. |
| 6,120,453 | A | 9/2000 | Sharp |
| 6,190,320 | B1 | 2/2001 | Lelong |
| 6,213,958 | B1 | 4/2001 | Winder |
| 6,231,585 | B1 | 5/2001 | Takahashi et al. |
| 6,280,387 | B1 | 8/2001 | Deforge et al. |
| 6,537,233 | B1 | 3/2003 | Rangayyan et al. |
| 6,569,098 | B2 | 5/2003 | Kawchuk |
| 6,585,651 | B2 | 7/2003 | Nolte et al. |
| 7,454,242 | B2 | 11/2008 | Fear et al. |
| 7,660,623 | B2 | 2/2010 | Hunter et al. |
| 7,676,023 | B2 | 3/2010 | Lang |
| 7,678,052 | B2 | 3/2010 | Torp et al. |
| 7,684,846 | B2 | 3/2010 | Johnson et al. |
| 7,769,422 | B2 | 8/2010 | DiSilvestro et al. |
| 7,920,731 | B2 | 4/2011 | Moreau-Gobard |
| 7,949,386 | B2 | 5/2011 | Buly et al. |
| 8,089,417 | B2 | 1/2012 | Popovic et al. |
| 8,265,728 | B2 | 9/2012 | MacMahon et al. |
| 8,444,564 | B2 | 5/2013 | Mahfouz et al. |
| 8,989,460 | B2 * | 3/2015 | Mahfouz ............... A61F 2/4003 382/128 |
| 2002/0082668 | A1 | 6/2002 | Ingman |
| 2005/0093859 | A1 | 5/2005 | Sumanaweera et al. |
| 2005/0165284 | A1 | 7/2005 | Gefen |
| 2005/0240098 | A1 | 10/2005 | Zhong et al. |
| 2006/0052727 | A1 | 3/2006 | Palestrant |
| 2007/0021738 | A1 | 1/2007 | Hasser et al. |
| 2007/0282200 | A1 | 12/2007 | Johnson et al. |
| 2007/0287900 | A1 | 12/2007 | Breen et al. |
| 2008/0009722 | A1 | 1/2008 | Simopoulos et al. |
| 2008/0094396 | A1 | 4/2008 | Sabczynsdi et al. |
| 2009/0003675 | A1 | 1/2009 | Moreau-Gobard |
| 2009/0015832 | A1 | 1/2009 | Popovic et al. |
| 2009/0018445 | A1 | 1/2009 | Schers et al. |
| 2009/0129652 | A1 | 5/2009 | Zwim et al. |
| 2009/0137907 | A1 | 5/2009 | Takimoto et al. |
| 2009/0226058 | A1 * | 9/2009 | Li ........................... G06T 7/149 382/128 |
| 2010/0022888 | A1 | 1/2010 | George et al. |
| 2010/0100011 | A1 | 4/2010 | Roche |
| 2010/0198067 | A1 | 8/2010 | Mahfouz |
| 2010/0234770 | A1 | 9/2010 | Colombet et al. |
| 2010/0256504 | A1 | 10/2010 | Moreau-Gaudry et al. |
| 2010/0277241 | A1 | 11/2010 | Moldsvor et al. |
| 2011/0054313 | A1 | 3/2011 | Kiyan |
| 2011/0125016 | A1 | 5/2011 | Lazebnik et al. |
| 2011/0305379 | A1 * | 12/2011 | Mahfouz ................ G16H 50/50 382/131 |
| 2011/0319755 | A1 | 12/2011 | Stein et al. |

FOREIGN PATENT DOCUMENTS

| | | | |
|---|---|---|---|
| WO | 2010088696 | | 8/2010 |
| WO | WO2010099359 | * | 9/2010 ............... A61F 2/00 |
| WO | 2010088696 | | 8/2011 |
| WO | 2012018851 | | 11/2011 |
| WO | 2012018851 | | 2/2012 |
| WO | 2012018851 | | 10/2012 |
| WO | 2013025613 | | 10/2012 |
| WO | 2013056231 | | 1/2013 |
| WO | 2013025613 | | 2/2013 |
| WO | 2013056231 | | 4/2013 |
| WO | 2013025613 | | 2/2014 |
| WO | 2013056231 | | 4/2014 |
| WO | 2014121244 | | 4/2014 |
| WO | 2014150961 | | 7/2014 |
| WO | 2014121244 | | 8/2014 |
| WO | 2014150780 | | 9/2014 |
| WO | 2014150961 | | 9/2014 |
| WO | 2014121244 | | 8/2015 |
| WO | 2014150780 | | 9/2015 |
| WO | 2014150961 | | 9/2015 |

OTHER PUBLICATIONS http://www.ultrasonix.com/wikisonix/index.php/Receiving_Ultrasound_Data.

Fleute et al, Incorporating a Statistically Based Shape Model Into a System for Computer-Assisted Anterior Cruciate Ligament Surgery, Medical Image Analysis 1999 vol. 3, No. 3.

European Patent Office, "Supplementary Search Report and Search Opinion", in published European Patent 2391971, dated Sep. 21, 2015, 10 pp.

European Patent Office, "Examination Report", in published European Patent 2391971, dated Apr. 19, 2018, 8 pp.

European Patent Office, "Supplementary Search Report and Search Opinion", in published European Patent 2741674, dated Mar. 9, 2015, 7 pp.

European Patent Office, "Supplementary Search Report and Search Opinion", in published European Patent 2765919, dated Jul. 3, 2015, 7 pp.

European Patent Office, "Supplementary Search Report and Search Opinion", in published European Patent 2950712, dated Aug. 18, 2016, 10 pp.

European Patent Office, "Supplementary Search Report and Search Opinion", in published European Patent 2967353, dated Oct. 6, 2016, 8 pp.

European Patent Office, "Examination Report", in published European Patent 2967353, dated Sep. 15, 2017, 4 pp.

European Patent Office, "Supplementary Search Report and Search Opinion", in published European Patent 2967440, dated Sep. 12, 2016, 7 pp.

European Patent Office, "Examination Report", in published European Patent 2967440, dated Dec. 11, 2018, 6 pp.

European Patent Office, "Supplementary Search Report and Search Opinion", in published European Patent 3213682, dated Jul. 17, 2017, 7 pp.

European Patent Office, "Search Report and Search Opinion", in European Divisional Patent Application 19162658.9, dated Jul. 15, 2019, 13 pp.

Wei Dong et al, "A Low-Cost Motion Tracker and Its Error Analysis", 2008 IEEE International Conference on Robotics and Automation, The Half-Day Workshop on: Towards Autonomous Agriculture of Tomorrow, May 19, 2008, 6 pp.

Angelo Maria Sabatini, "Estimating Three-Dimensional Orientation of Human Body Parts by Inertial/Magnetic Sensing", Sensors, vol. 11, No. 2, Jan. 1, 2011, 37 pp.

* cited by examiner

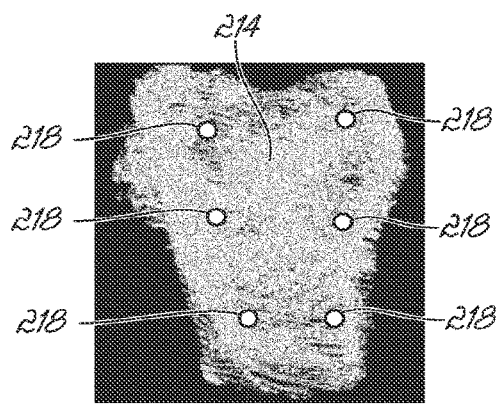
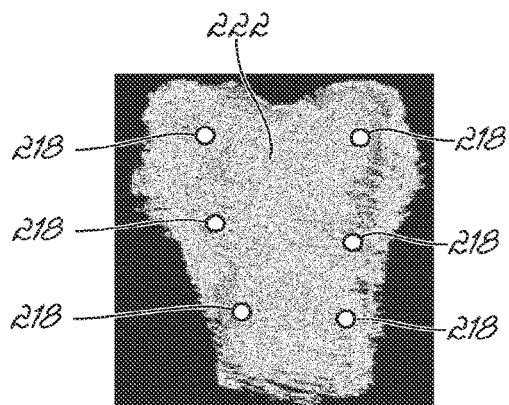
FIG. 16A  FIG. 16B
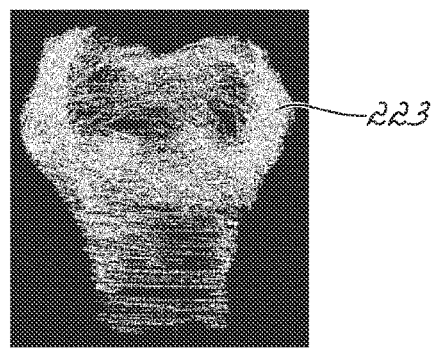
FIG. 16C
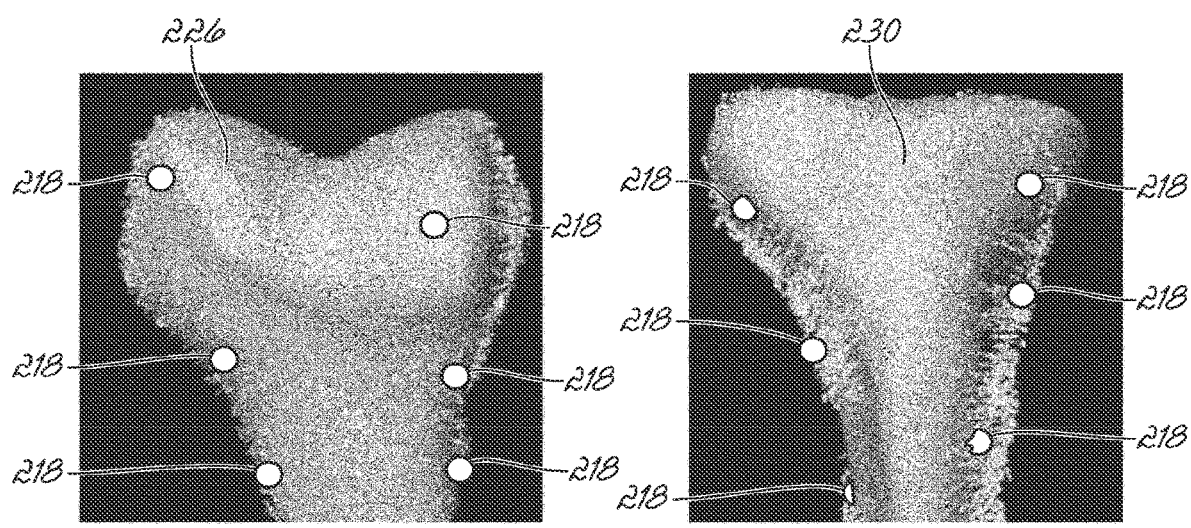
FIG. 16D  FIG. 16E

REAL-TIME 3-D ULTRASOUND RECONSTRUCTION OF KNEE AND ITS IMPLICATIONS FOR PATIENT SPECIFIC IMPLANTS AND 3-D JOINT INJECTIONS

CROSS-REFERENCE TO RELATED APPLICATIONS

This application is a continuation of U.S. Nonprovisional patent application Ser. No. 14/250,957, filed Apr. 11, 2014, titled "Real-Time 3-D Ultrasound Reconstruction of Knee and Its Implications For Patient Specific Implants and 3-D Joint Injections," which is a continuation of and claims priority to International Application No. PCT/US2012/60261, titled "REAL-TIME 3-D ULTRASOUND RECONSTRUCTION OF KNEE AND ITS IMPLICATIONS FOR PATIENT SPECIFIC IMPLANTS AND 3-D JOINT INJECTIONS," filed Oct. 15, 2012, which claims the benefit of and priority to U.S. Provisional Application Ser. No. 61/547,508, filed on Oct. 14, 2011 and titled REAL-TIME 3-D ULTRASOUND RECONSTRUCTION OF KNEE AND ITS IMPLICATIONS FOR PATIENT SPECIFIC IMPLANTS AND 3-D JOINT INJECTIONS, the disclosures of which are hereby incorporated by reference in their entireties.

TECHNICAL FIELD

The invention relates generally to real-time imaging of joints using non-ionizing imaging methods, and more particularly to the use of real-time imaging to plan surgical procedures, including guiding needles during joint injection treatment procedures.

BACKGROUND

Joint pain is a major public health problem and is responsible for significant costs and disability in the United States. This is due, at least in part, to underlying osteoarthritis. Joint pain occurs in approximately 46 million Americans and is increasing due to an aging population and an epidemic of increasing obesity. Joint pain costs the healthcare system about $37 billion annually. Depending on the degree of patient disability, joint pain can be treated with a range of systemic and targeted interventions. Systemic interventions include over the counter medications, physical therapy, prescription pain relievers and anti-inflammatory medications (e.g. Naprosyn). Targeted interventions include injection of medications into the affected joint, arthroscopic surgical correction of underlying pathology and ultimately total joint replacement surgery. Within the targeted interventions segment, there are approximately 10 million patients in the United States receiving injection treatments of the knee, hip, spine, and shoulder. Many of these treatments involve expensive pre-arthroplasty substances, such as single dose visco-supplements, platelet rich plasma, stem cells, etc. These substances are typically injected without needle guidance assistance so that delivery accuracy depends entirely on the skill of the physician. Studies have revealed injection inaccuracies ranging from 18-34% in the knee and 33-90% in the shoulder, with similar missed injection rates in the hip. Failure of these conservative treatments result in an estimated 505,000 knee, 280,000 hip and 42,000 shoulder replacements (arthroplasty) annually in the United States alone. By 2030, the number of knee and hip arthroplasties are projected to increase by 565% and 101% respectively. For every joint replacement patient there are an estimated 10 patients upstream in the care pathway creating a large symptomatic population that is projected to increase 40% by 2030.

A major challenge for conservative management of joint pain is the lack of low cost, accurate, non-ionizing joint imaging technology. A low-cost imaging modality to accurately visualize joints would represent a significant musculoskeletal innovation relative to fluoroscopy or MRI imaging. Moving diagnostic and treatment to lower-cost sites (e.g., from hospital to office-based) and providers (e.g., from radiologist to physicians and physician assistants) is necessary if costs are to be contained as injection substance cost and joint pain numbers increase. Today, knee and shoulder injections are office-based procedures only for skilled orthopedists or musculoskeletal specialists. Improved joint visualization would enable accurate treatment of most joints by lower cost providers in the office. Improved joint visualization and injection efficacy, as well as the migration of many injections to lower-cost settings and providers, is also attractive to third-party payers.

Office X-Rays show only a 2-D image of joint space and offer minimal bony and/or soft-tissue anatomic data. Ultrasound is widely accepted as a means to visualize the joint space, but the present technology has significant limitations. Current ultrasound-based joint injection guidance systems provide orthopedic surgeons with a difficult-to-interpret 2-D planar image of a limited area of the joint to be injected. In the joint orientation which provides the best joint space visualization, the needle is often perpendicular to the probe and seen only as a spot. Some surgeons use fluoroscopy to assist with the guidance, which can be harmful to both the patient and the surgeon due to the ionizing X-Ray radiation emitted. These images are also typically distorted, and require distortion correction. The resulting corrected 2-D images can be quite blurry. To limit the amount of radiation exposure, many surgeons do not keep the fluoroscopy machine active to track the needle while the needle is being inserted into the joint. Rather, the surgeon captures snapshots of the joint at different time intervals in order to obtain the location of the needle relative to the joint space. But, even with these modified techniques, fluoroscopy exposes the patient to X-Ray radiation far in excess of conventional radiographs. Injections with these modalities are also typically more painful if multiple injection attempts or needle repositioning is needed to correct inaccuracies in the injections due to a lack of real-time imaging to help guide the needle.

MRI scans are conducted under static conditions and are often difficult to interpret. The inability to allow metal objects near the joint during an MRI, and the confined area in which the patient is placed further limits the ability of MRI to provide real time imaging during the injection. MRI procedures are also very expensive, and may reveal multiple concerns, which makes it difficult for the physician to make a proper diagnosis.

Most medical practices also cannot afford fluoroscopic or MRI guided equipment, so almost all joint treatment that involves imaging of the joint is performed at an outpatient facility or hospital. These imaging modalities also require additional room shielding and regulatory oversight, as well as expensive specialized personnel.

Therefore, there is a need for a joint imaging and injection modality that overcomes the foregoing limitations. More specifically, there exists a need for joint injection guidance systems that do not require X-Ray radiation exposure and that provide real-time tracking of the needle on its approach to the joint space.

SUMMARY

In an embodiment of the invention, a method for treating a patient is presented. The method includes acquiring a plurality of radio frequency (RF) signals with an ultrasound transducer, with each RF signal representing a return signal from a scan line of a pulse-mode echo ultrasound scan. The method determines a position of the ultrasound transducer corresponding to each of the acquired RF signals and generates a plurality of contour lines from the plurality of RF signals. The method further includes and estimating a 3-D shape and position of an anatomical feature of the patient based on the generated contour lines and corresponding ultrasound transducer positions.

In another embodiment of the invention, an apparatus for treating a patient is presented. The apparatus includes a processor and a memory containing instructions that are executed by the processor. When the instructions are executed by the processor, the instructions cause the apparatus to acquire a plurality of radio frequency (RF) signals with an ultrasound transducer, each RF signal representing a return signal from a scan line of a pulse-mode echo ultrasound scan. The instructions also cause the apparatus to determine a position of the ultrasound transducer corresponding to each of the acquired RF signals and generate a plurality of contour lines from the plurality of RF signals. The instructions further cause the apparatus to estimate a 3-D shape and position of an anatomical feature of the patient based on the generated contour lines and corresponding ultrasound transducer positions.

BRIEF DESCRIPTION OF THE DRAWINGS

The accompanying drawings, which are incorporated in and constitute a part of this specification, illustrate embodiments of the invention and, together with a general description of the invention given below, serve to explain the principles of the invention.

FIGS. 16A-16E are diagrammatic views illustrating a 3-D joint model being generated from a point cloud of a joint obtained using ultrasound scan lines.

DETAILED DESCRIPTION

Figure 1:
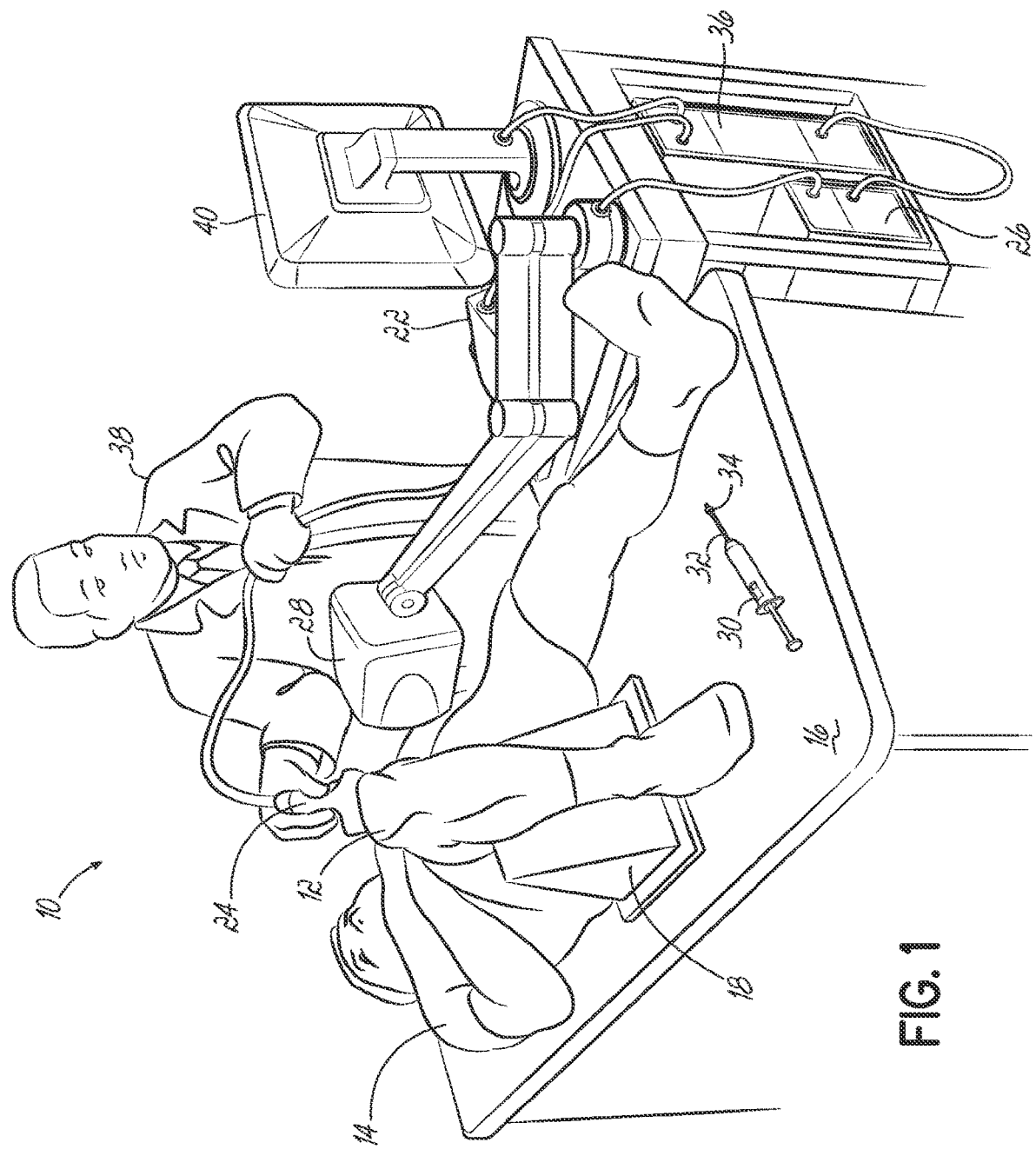
FIG. 1 is a perspective view of an injection suite with a patient lying in a supine position.

The present invention overcomes the foregoing problems and other shortcomings, drawbacks, and challenges of conventional joint visualization modalities and injection protocols. Embodiments of the invention provide a patient-specific 3-D view of the joint bones and joint space that reduces the skill level required to perform joint injection procedures. The targeted location for the injection, or desired injection point, can also be designated in the 3-D view. This designation allows for a 3-D vector depicting distance to the target and/or a 3-D distance map to be displayed, allowing for the end of the needle to be precisely placed in an optimal position within the joint. This optimal needle placement will help ensure that the injected material is delivered in a proper position. Needle injection using real-time ultrasound guidance with 3-D joint visualization may improve injection accuracy, reduce time spent on joint injections, reduce the cost and complexity of the process, and reduce the pain and discomfort to patients caused by multiple or missed injection attempts. Moreover, while the invention will be described in connection with certain embodiments, it will be understood that the invention is not limited to these embodiments. To the contrary, this invention includes all alternatives, modifications, and equivalents as may be included within the spirit and scope of the present invention.

Therapeutic injections of joints can benefit from three-dimensional ("3-D") needle guidance to ensure optimal placement within the joint. By scanning the knee with ultrasound, patient-specific bones can be modeled, one example of which is shown and disclosed in International Patent Application No. PCT/US11/46318, entitled "METHOD AND APPARATUS FOR THREE DIMENSIONAL RECONSTRUCTION OF A JOINT USING ULTRASOUND", the disclosure of which is incorporated herein by reference in its entirety. Briefly, 3-D bone models are registered to the patient's bone position as the leg is secured in a series of fixed positions. In accordance with the invention, the injection needle may be tracked using an electromagnetic tracker or any other suitable tracking technology, such as optical tracking. The position of these sensors could be multi-factorial, but one example would on the external handle of the needle that the physician holds on to while administering the injection. The 3-D model of the patient's knee joint is then visualized showing needle motion relative to the joint space, and is continuously updated as the needle advances and the injection is completed. For example, a red dotted line extending from the needle may be shown on a monitor in response to detecting contact between the needle and the patient's skin. This line may help the physician visualize how to guide the needle, and may be calculated and recalculated in real-time with every detected motion of the needle so that the line is continually updated. In response to determining that a clear path exists between the needle and the desired injection point, the appearance of the displayed line may be changed, such as by changing the color from red to green, to indicate to the physician that the needle has a clear path.

Although the embodiments of the invention described herein are focused on knee joint injections, persons having ordinary skill in the art will recognize that other joint injections could also benefit from 3-D guidance. These joints include, but are not limited to the shoulder, hip, spine, sacroiliac, elbow, wrist and hands, for example. Moreover, persons having ordinary skill in the art will further understand that bursae, tendon, and other musculoskeletal and soft tissue injections could similarly benefit from 3-D ultrasound real-time guidance. Embodiments of the invention are therefore not limited to the treatment of knees or joints.

Figure 2:
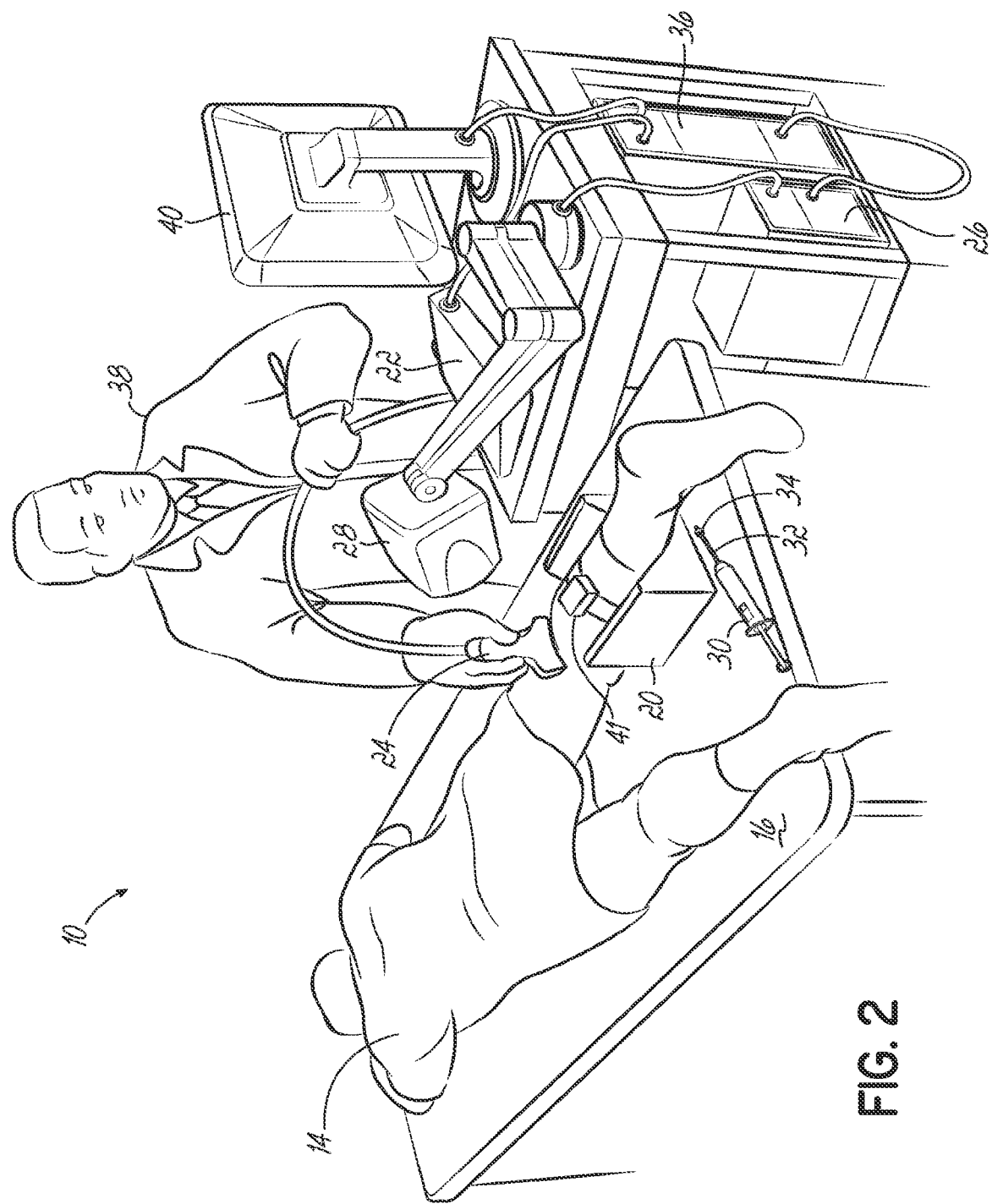
FIG. 2 is a perspective view of the injection suite in FIG. 1 with the patient lying in a prone position.

Referring now to FIGS. 1 and 2, an injection suite 10 for treating a joint, such as a knee joint 12 of a patient 14, includes an exam table 16, a first leg positioner 18 for use in the supine position, a second leg positioner 20 for use in the prone position, and installation equipment (not shown) to fix the first and second leg positioners 18, 20 to the table 16 as desired or necessary. The treatment suite 10 also includes an ultrasound machine 22 having a treatment head or transducer 24, an electromagnetic tracking system 26 that includes an electromagnetic transceiver unit 28, and a syringe 30 for applying the injection that includes a needle 32 having a tracking device or element 34. The ultrasound machine 22 and electromagnetic tracking system 26 are operatively coupled to a computer 36, which provides real-time visual feedback to a treating physician 38 via a monitor 40 based on signals from the ultrasound machine 22 and/or electromagnetic tracking system 26. Other joints and types of musculoskeletal injections may require specific positioning stabilization methodologies and devices other than those shown in FIGS. 1 and 2.

A first series of scans may be performed using the ultrasound machine 22 by positioning the transducer 24 (which may include an array of transducers) on the joint 12 of patient 14 to begin creating a 3-D joint image in the computer 36. For imaging the anterior portion of the joint 12, and as is shown in FIG. 1, the patient 12 is placed in the supine position on the exam table 16 with the first positioner 18, shown in FIG. 1 as a specialized wedge, placed firmly against the buttocks of the patient 12. Although the patient is supine in this figure, other non weight-bearing or weight-bearing positions could also be used for the procedure. The joint 12 to be treated with an injection is exposed and free of clothing. The joint 12 is bent over the first positioner 18 to achieve a deep knee bend, and may be held in place against the first positioner 18 by thigh and shin straps (not shown). The position of the patient's leg should be stable and secure while achieving the maximum comfortable flexion of the joint 12.

Optionally, one or more motion sensors 41, such as a sensor including one or more accelerometers configured to detect 6-degrees of motion may be secured on the posterior side of the joint 12. This motion sensor may be placed within a skin fold created by bending the joint 12, or by strapping the motion sensor to the patient's leg as shown in FIG. 2. By including the one or more motion sensors 41, the coordinates of the injection point may be determined and saved by the computer 36. The physician 38 could then ask the patient 14 how they feel after a first injection. If the patient responds positively, the physician 38 could then use the coordinates from the initial injection to administer another injection in the same location as the previous injection. A sterile drape with sensors and openings to provide access to the skin for scanning could also be used to detect motion.

The boundaries of the joint 12 are palpated and, optionally, these boundaries may be marked with a skin marker for future reference. The distance between the closest femoral location to be scanned and the center of the electromagnetic transceiver unit 28 should range from about 20 to about 25 cm. To improve acoustic coupling between the transducer 24 and the patient 14, ultrasound gel is normally applied liberally to the joint 12 in preparation for scanning.

Figure 3:
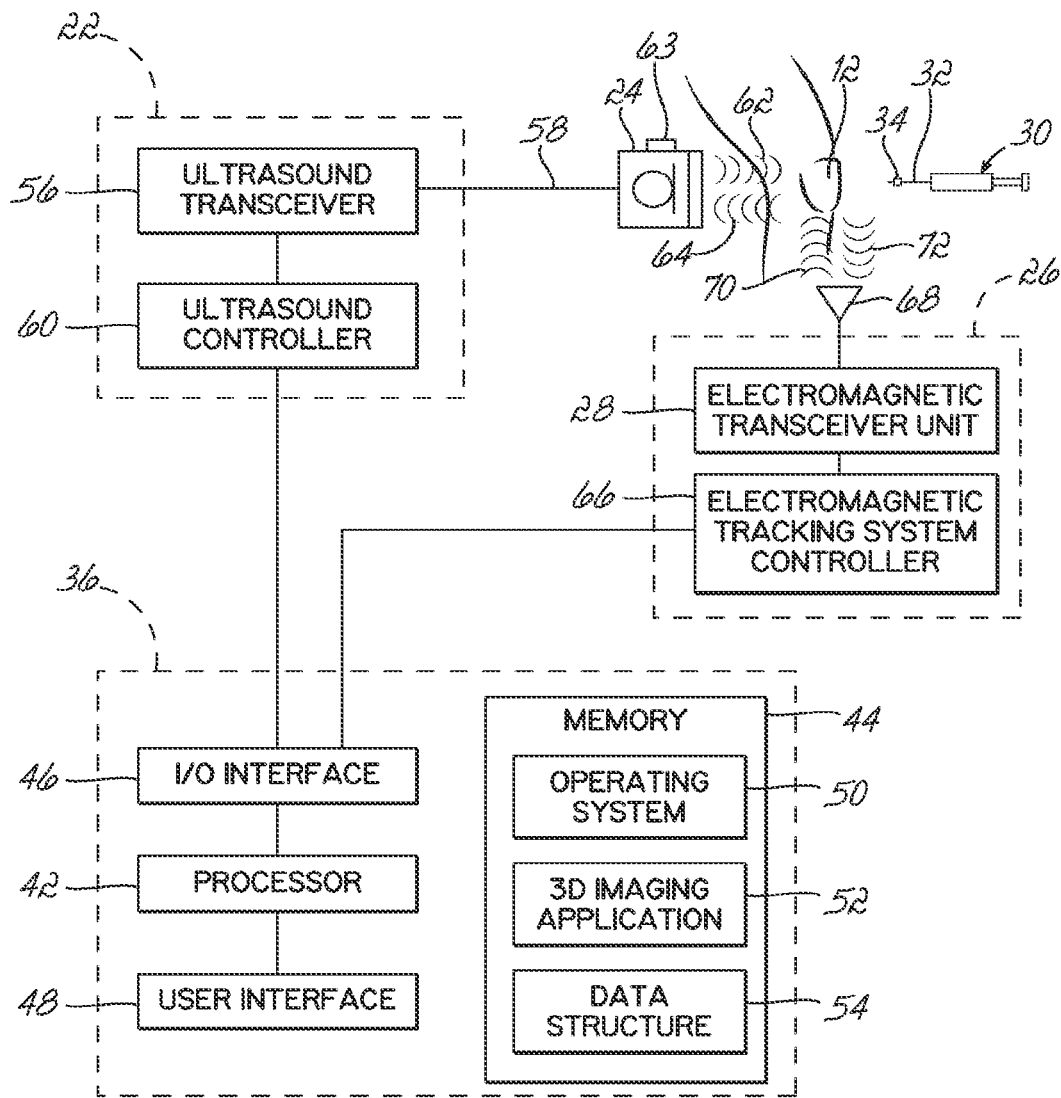
FIG. 3 is a diagrammatic view of a medical imaging system including an ultrasound machine, electromagnetic tracking system, and a computer that operate cooperatively to provide real-time 3-D images to the attending physician.

Referring now to FIG. 3, the ultrasound machine 22, electromagnetic tracking system 26, and computer 36 are shown in more detail. The computer 36 includes a processor 42, a memory 44, an input/output (I/O) interface 46, and a user interface 48. The processor 42 may include one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 44. Memory 44 may be a single memory device or a plurality of memory devices including but not limited to read-only memory (ROM), random access memory (RAM), volatile memory, non-volatile memory, static random access memory (SRAM), dynamic random access memory (DRAM), flash memory, cache memory, or any other device capable of storing information. Memory 44 may also include a mass storage device (not shown) such as a hard drive, optical drive, tape drive, or non-volatile solid state device. Moreover, memory 44 may include remotely located memory or mass storage devices in communication with the computer via a network or other communications link.

Processor 42 may operate under the control of an operating system 50 that resides in memory 44. The operating system 50 may manage computer resources so that computer program code embodied as one or more computer software applications, such as a 3-D imaging application 52 residing in memory 44, may have instructions executed by the processor 42. In an alternative embodiment, the processor 42 may execute applications 52 directly, in which case the operating system 50 may be omitted. One or more data structures 54 may also reside in memory 44, and may be used by the processor 42, operating system 50, and/or 3-D imaging application 52 to store or register data, such as ultrasound image data, ultrasound scan data, and/or needle position data.

The I/O interface 46 operatively couples the processor 42 to other devices and systems in the injection suite 10, including the ultrasound machine 22 and electromagnetic tracking system 26. The I/O interface 46 may include signal processing circuits that condition incoming and outgoing signals so that the signals are compatible with both the processor 42 and the components to which the processor 42 is coupled. To this end, the I/O interface 46 may include analog-to-digital (A/D) and/or digital-to-analog (D/A) converters, voltage level and/or frequency shifting circuits, optical isolation and/or driver circuits, and/or any other analog or digital circuitry suitable for coupling the processor 42 to the other devices and systems in the treatment suite 10. For example, the I/O interface 46 may include one or more amplifier circuits to amplify signals received from the ultrasound machine 22 prior to analysis in the computer 36.

The user interface 48 includes the monitor 40, and is operatively coupled to the processor 42 of computer 36 in a known manner to allow the physician 38 to interact directly with the computer 36. In addition to the monitor 40, the user interface 48 may include video and/or alphanumeric displays, a touch screen, a speaker, and any other suitable audio and visual indicators capable of providing information to the system operator. The user interface 48 may also include input devices and controls such as an alphanumeric keyboard, a pointing device, keypads, pushbuttons, control knobs, microphones, etc., capable of accepting commands or input from the system operator and transmitting the entered input to the processor 42. In this way, the user interface 48 may enable manual initiation of system functions, for example, during set-up of the system, or to view or manipulate images.

The ultrasound machine 22 may include an ultrasound transceiver 56 operatively coupled to the transducer 24 by a cable 58, and a controller 60. The ultrasound transceiver 56 generates drive signals that excite the transducer 24 so that the transducer 24 generates ultrasound signals 62 that can be transmitted into the patient 14. In an embodiment of the invention, the ultrasound signals 62 comprise bursts or pulses of ultrasound energy suitable for generating ultrasound images. The transducer 24 may also include a tracking device, such as an electromagnetic or optical tracking element 63.

Reflected ultrasound signals, or echoes 64, are received by the transducer 24 and converted into RF signals that are transmitted to the transceiver 56. Each RF signal may be generated by a plurality of echoes 64, which may be isolated, partially overlapping, or fully overlapping. Each of the plurality of echoes 64 originates from a reflection of at least a portion of the ultrasound energy at an interface between two tissues having different densities, and represents a pulse-echo mode ultrasound signal. One type of pulse-echo mode ultrasound signal is known as an "A-mode" scan signal. The controller 60 converts the RF signals into a form suitable for transmission to the computer 36, such as by digitizing, amplifying, or otherwise processing the signals, and transmits the processed RF signals to the computer 36 via the I/O interface 46. In an embodiment of the invention, the signals transmitted to the computer 36 may be raw RF signals representing the echoes 64 received by the transducer 24.

The electromagnetic tracking system 26 includes the electromagnetic transceiver unit 28 and an electromagnetic system controller 66. The transceiver unit 28 may include one or more antennas 68, and transmits a first electromagnetic signal 70. The first electromagnetic signal 70 excites the tracking element 34, which responds by transmitting a second electromagnetic signal 72 that is received by the transceiver 28. The tracking system controller 66 may then determine a relative position of the tracking element 34 based on the received second electromagnetic signal 72. The system controller 66 may then transmit tracking element position data to the computer 36 via I/O interface 46.

In the example for knee joint imaging and eventual injection illustrated in FIGS. 1 and 2, the ultrasound transducer 24 is placed proximate the lateral epicondyle, with the ultrasound transducer 24 in the long axis orientation. In the long axis orientation, the ultrasound transducer 24 is aligned with the axis of the leg and moved from medial to lateral. Ultrasound data acquisition is started in the 3-D imaging application 52 of computer 36, and the ultrasound transducer 24 is moved in a circumferential motion, back and forth towards the femoral shaft. Ultrasound data is thereby acquired from the caudal and cranial and anterior and lateral femur. Once a sufficient amount of ultrasound data points have been collected, the ultrasound transducer 24 is moved to the medial epicondyle. The medial epicondylar femoral region is then scanned, in a similar manner, to acquire a sufficient number of data points corresponding individual bone echoes to reconstruct the anteromedial femur.

It is preferable to reduce patient motion as much as possible during scan acquisition to optimize the acquired data. The optional motion sensor(s) 41 described above may be used to alert the physician 38 if a motion threshold has been met, or to temporarily suspend data collection by the application 52 in response to detecting motion, thereby improving overall imaging accuracy. Scans may be repeated by pausing and resuming the scan until a sufficient point density is achieved. When scanning the femur, care should be taken to avoid scanning of the tibia, the fibula, and/or the patella. When a sufficient point density achieved, the imaging application 52 may stop acquiring data and the data saved to memory 44. Different knee joint flexion positions may also be utilized to optimize surface topographic resolution.

In preparation for anterior tibial scanning, the electromagnetic transceiver unit may be positioned about 30 cm to about 35 cm from the closest tibial region to be scanned. Additional ultrasound gel may be applied to the tibia, as desired or necessary. Using a long axis ultrasound transducer orientation, the acquisition program is started and the lateral side of the tibia, anterior to the fibula, is scanned. The fibula should not be included in the scans, and contact between the ultrasound transducer 24 and the electromagnetic transceiver unit 28 should be avoided. The ultrasound transducer 24 should be oriented perpendicular to the skin surface of the patient 14 as the transducer 24 is swept circumferentially, back and forth, towards the anterior surface. The ultrasound transducer 24 is brought towards the medial side while in the long axis orientation. Once a sufficient point cloud density has been achieved, the data is saved in memory 44 by the application 52, either automatically or in response to user interaction with the user interface 48. Data collection by the application 52 may be paused and/or resumed as necessary while ultrasound data is being collected. It may also be advantageous to reorient the patient 14 so that the joint 12 achieves other degrees of flexion or rotation to fill in areas of the tibial bone or joint contour. In this way, desired data enhancement may be obtained to fill a specific need, such as to design or optimize position and fit of patient specific bone cutting guides.

The tibial plateau is scanned using a short axis ultrasound transducer orientation, including angling of the ultrasound transducer to aid in visualization. Pressure may be required to adequately scan this region. Frequent saving of the data prevents data loss due to, for example, leg movement. To this end, the application 52 may be configured to periodically save the data to memory 44 automatically. After an adequate amount of point cloud data has been acquired, the application 52 may be stopped or paused, and the data saved to memory 44.

The patient may be prepared for posterior scanning, as best shown in FIG. 2, by placing the patient in the prone position. To reposition the patient 14, the first positioner 18 is removed from the table 16, and the second positioner 20, shown as a leg cradle, is fixed to the table 16. In another embodiment of the invention, the injection suite 10 may include more than one exam table 16, with one exam table 16 configured for supine positioning of the patient 14, and another exam table 16 configured for prone positioning of the patient 14. In this alternative embodiment, the patient 14 may merely move to the second table 16 prior to posterior scanning.

In any case, the patient 14 lies in the prone position with the leg of interest placed in the second positioner 20 and the opposite leg spread to allow medial access to the leg of interest. The leg may be firmly held into place with straps (not shown) to minimize movement. The posterior aspect of the femur is palpated toward the lateral side until the edge of the fibula is located and is outline marked. The bony boundaries within the joint are palpated and, optionally, marked with a skin marker. Optionally, the motion sensor(s) 41 may be secured to the anterior side of the knee joint 12 on the patellar surface. In an alternative embodiment, a holed posterior knee drape with embedded sensors may also be used to detect motion of the leg. Ultrasound gel may be applied liberally and evenly onto the regions of the knee joint 12 to be scanned.

To scan the femur, the ultrasound transducer 24 is oriented with the long axis perpendicular to the long axis of the leg. In cases where the ultrasound transducer 24 is symmetric, one side may be marked so that the ultrasound transducer 24 can be positioned correctly with the appropriate side pointing distally during this stage of scanning. The medial and lateral condyles are identified and the ultrasound transducer 24 is moved, distally, until the condyle is at the top of the display 40. Optionally, the medial and lateral condyles may be marked with a skin marker. Again, with a long axis ultrasound transducer orientation, the medial condyle is scanned circumferentially, back and forth, tilting the ultrasound transducer 24 as necessary, but avoiding excessive tilt to reduce the potential for imaging error. This process may then be repeated on the lateral condyle or on either condyle until sufficient data points are gathered, pausing and restarting as necessary or desired. Care should be taken not to induce a jerking reflex when scanning the lateral condyle so that the knee joint 12 may be kept still during scanning. After a sufficient amount of point cloud data has been generated, the application 52 may be stopped or paused and the data saved to memory 44. To further advance the process, a timed data saving procedure could be used so that the application 52 automatically saves the data based on specifications defined by the user of the system. These specifications may be entered, for example, via the user interface 48.

The electromagnetic transceiver unit 28 may be repositioned for the posterior tibial scans. The transceiver unit 28 should be placed about 30 cm to about 35 cm from the closest tibial surface to be scanned, and contact between the ultrasound transducer 24 and the transceiver unit 28 should be avoided during any scanning activity. Adequate ultrasound gel coverage should be ensured. With a long axis probe orientation, the ultrasound transducer 24 is positioned on the lateral side posterior to the fibula, and the imaging application 52 started so that data is acquired while the ultrasound transducer 24 is moved circumferentially across the posterior surface of the leg. Preferably, the face of the ultrasound transducer 24 is kept perpendicular to the surface of the skin while the transducer 24 is being moved. The fibula should also be avoided while scanning the desired contiguous lateral tibia. This process may be repeated on the medial side of the leg, pausing as necessary or desired. The posterior tibial scan is continued until sufficient data has been gathered. The imaging application 52 may then be paused or stopped, and the acquired scan data saved to memory 44.

This process could also be conducted using multiple ultrasonic transducers 24, with each transducer 24 having unique features to optimize the transducer's performance for a specific function. Initially, the system user could utilize a general purpose transducer 24 that scans the joint. Then, a second transducer 24 that is more focused in nature could be used to either define specific geometries and/or define shapes that are partially occluded. A third, more sensitive transducer 24 could then be used to define defects, locate fractures, and possibly locate areas of concern for the physician before the needle injection procedure is attempted.

The ultrasound scanning process described herein could also be directed to a subset of a joint. For example, in the knee, a joint injection requires less accuracy than surgical treatment planning or fitting and design of patient specific bone cutting guides. Thus, it may not be necessary to scan all four surfaces of the knee for every clinical use of embodiments of the invention. Some applications may only require scanning the anterior or posterior or portions thereof. When scanning other joints, such as when guiding an injection in the subacromial bursa of the shoulder, it may only be necessary to scan portions of the humerus, acromion and clavicle and not every aspect of all the bones forming the shoulder.

Figure 4:
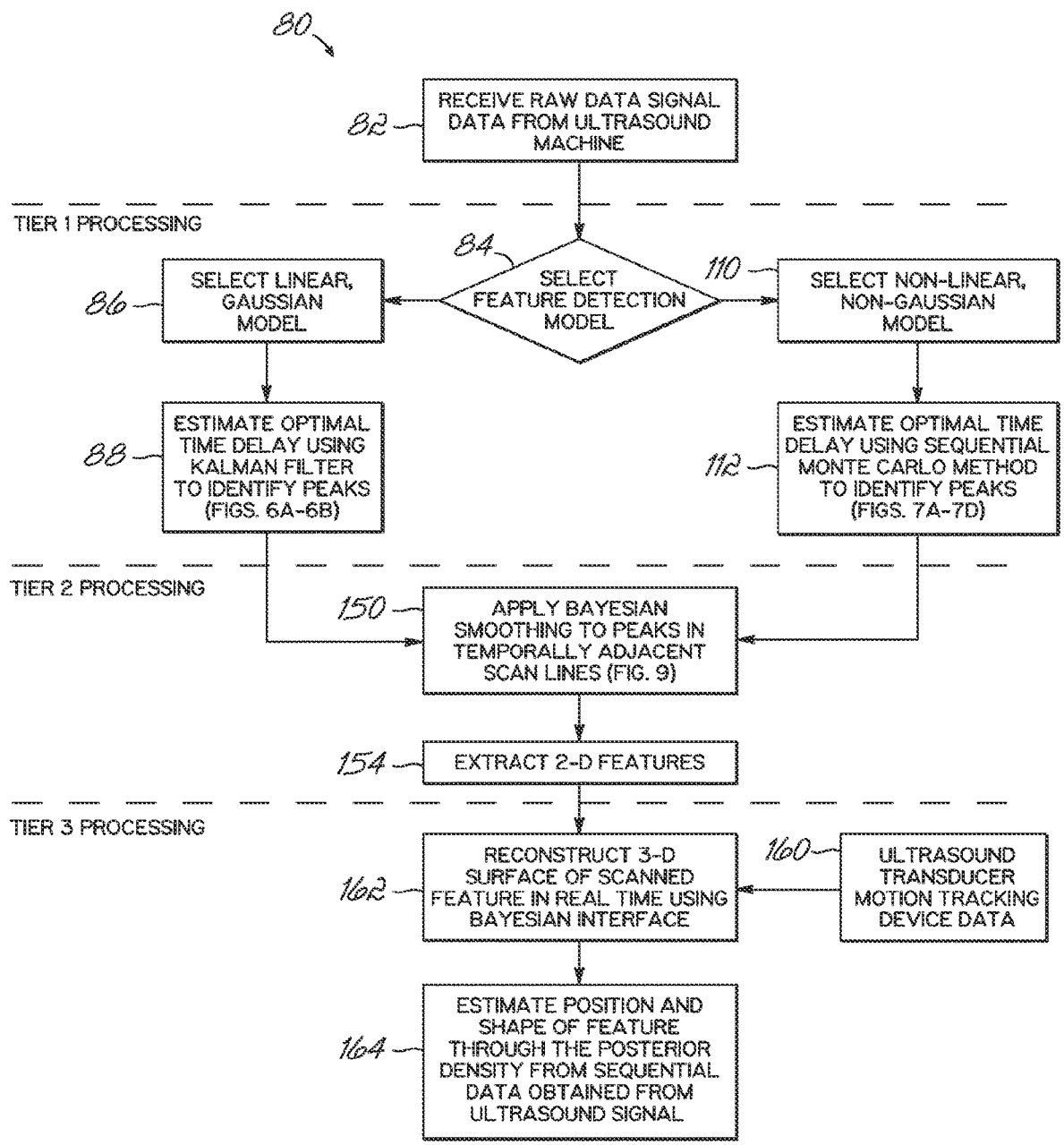
FIG. 4 is a flow chart illustrating one method by which the imaging system in FIG. 3 generates a real-time 3-D image.

Referring now to FIG. 4, a flow chart 80 illustrates an embodiment of the invention in which the acquired scan data is used to reconstruct patient-specific bone models. In one aspect of the invention, these bone models may be used to generate real time 3-D images that are used to assist the physician 38 in guiding a needle 32 to inject substances into a desired position in a joint 12 of a patient 14, as discussed in more detail below. The patient-specific bone models may be generated from raw RF signals that are used directly to automatically extract bone contours from ultrasound scans. Specifically, embodiments of the invention include methods of bone/cartilage contour detection, point cloud, and 3-D model reconstruction from ultrasound RF signal data. The ultrasound signal processing optimizes scan reconstruction through a three-tier signal processing model. The first tier optimizes the raw signal data and estimates the envelope of the feature vectors. The second tier estimates the features detected from each of the scan lines from the first tier, and constructs the parametric model for Bayesian smoothing. The third tier estimates the features extracted from the second tier to further estimate the three dimensional features in real-time using a Bayesian inference method.

Figure 5:
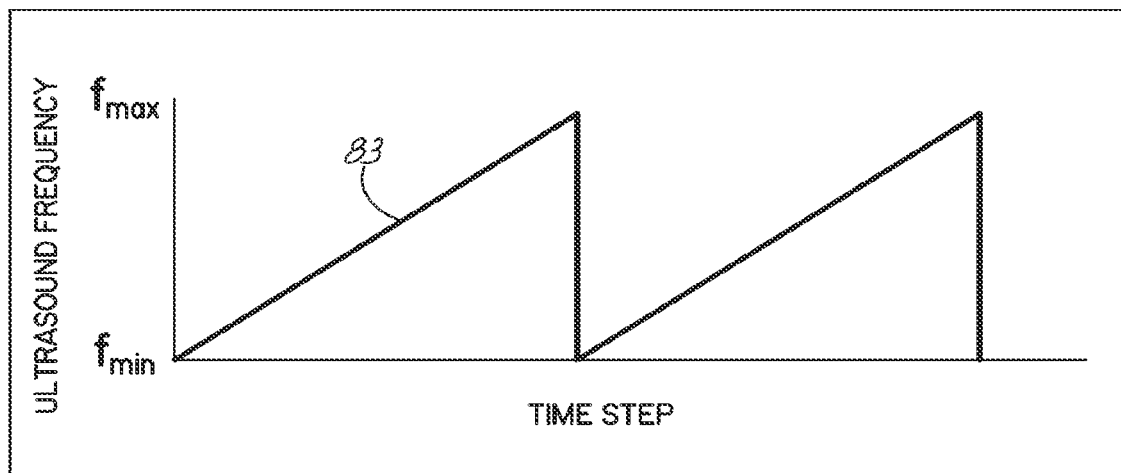
FIG. 5 is a graphical view illustrating an ultrasound signal that is swept in frequency.

In block 82, raw RF signal data representing ultrasound echoes 64 detected by the transducer 24 is received by the application 52 and processed by a first layer of filtering for feature detection. The feature vectors detected include bone, fat tissues, soft tissues, and muscles. The optimal outputs are envelopes of these features detected from the filter. There are two fundamental aspects of this design. The first aspect relates to the ultrasound transducer 24 and the ultrasound controller firmware. In conventional ultrasound machines, the transmitted ultrasound signals 62 are generated at a fixed frequency during scanning. However, it has been determined that different ultrasound signal frequencies reveal different joint features when used to scan the patient 14. Thus, in an embodiment of the invention, the frequency of the transmitted ultrasound signal 62 is swept with respect to time using a sweep function. One exemplary sweep function is a linear ramping sweep function 83, which is illustrated in FIG. 5.

Figure 6A:
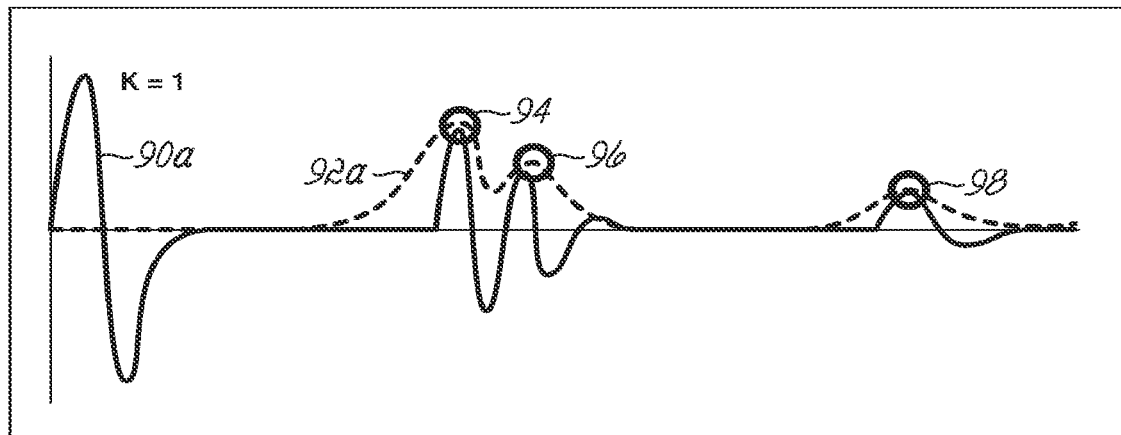
FIGS. 6A and 6B are graphical views illustrating an RF signal, a signal envelope generated from the RF signal, and a plurality of amplitude peaks identified in the signal envelope using a linear Gaussian filter.
Figure 6B:
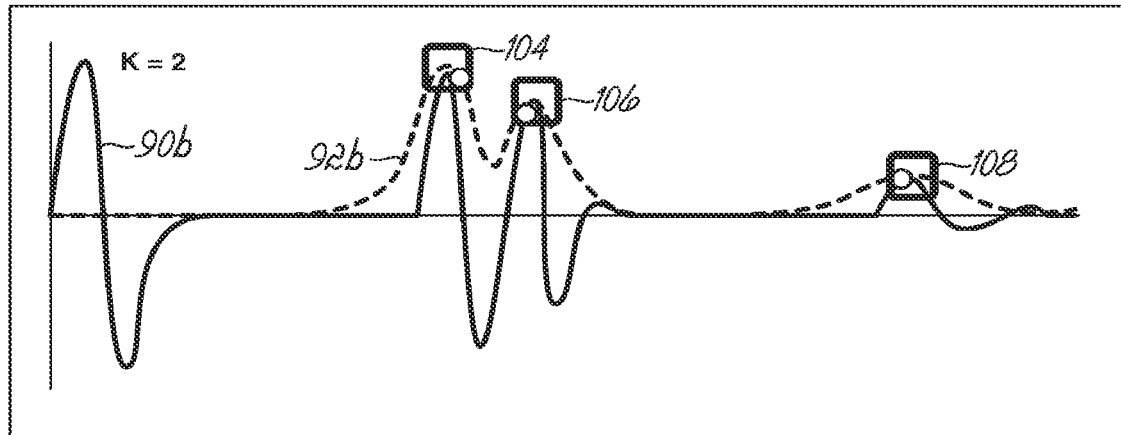

The second aspect is to utilize data collected from multiple scans to support a Bayesian estimation-correction algorithm. Two exemplary filter classes are illustrated in FIG. 4, either of which may be used support the estimation-correction algorithm. In decision block 84, the application 52 selects a feature detection model that determines the class of filter through which to process the RF signal data. If the data is to be processed by a linear filter, the application proceeds to block 86. In block 86, the imaging application 52 selects a linear class of filter, such as a linear Gaussian model based on the Kalman filter family, the operation of which is illustrated by FIGS. 6A and 6B. FIGS. 6A and 6B outline the basic operation of the Kalman filter, upon which other extensions of the filter are built.

In block 88, an optimal time delay is estimated using a Kalman filter to identify peaks in the amplitude or envelope of the RF signal. Referring now to FIG. 6A, at time k=1, the filter is initialized by setting the ultrasound frequency $f_k=f_1$. The received echo or RF signal ($s_{obs}$) is represented by plot line 90a, while the signal envelope is represented by plot line 92a. The peak data matrix ($p_{k,fk}$), which contains the locations of the RF signal peaks, may be calculated by:

$$p_{k,fk}=E(s_{obs}) \quad \text{(Equation 1)}$$

where E is an envelope detection and extraction function. The peak data matrix ($p_{k,fk}$) thereby comprises a plurality of points representing the signal envelope 92, and can be used to predict the locations of envelope peaks 94, 96, 98 produced by frequency $f_{k+1}$ using the following equation:

$$p_{est,fk+1}=H(p_{k,fk+1}) \quad \text{(Equation 2)}$$

where H is the estimation function.

Referring now to FIG. 6B, at time k=2, the filter enters a recursive portion of the imaging algorithm. To this end, the frequency of the transmitted ultrasound signal 62 is increased so that $f_k=f_2$, and a new RF signal is received ($s_{obs,fk}$), as represented by plot line 90b. The new RF signal 90b also generates a new signal envelope 92b. A peak data matrix is calculated ($p_{k,fk}$) for the new signal envelope 92b, which identifies another set of peaks 104, 106, 108. The error of the prediction is computed by:

$$\varepsilon=p_{est,fk-1}-p_{k,fk} \quad \text{(Equation 3)}$$

and the Kalman gain ($K_k$) is computed by:

$$K_k=P_k^- H^T(HP_k^- H^T+R) \quad \text{(Equation 4)}$$

where $P_k^-$ is the error covariance matrix, and R is the covariance matrix of the measurement noise. The equation for estimating the peak data matrix for the next cycle becomes:

$$p_{est,k+1}=p_{k,fk}+K_k(\varepsilon) \quad \text{(Equation 5)}$$

and the error covariance is updated by:

$$P_k=(I-K_k H)P_k^- \quad \text{(Equation 6)}$$

Figure 7A:
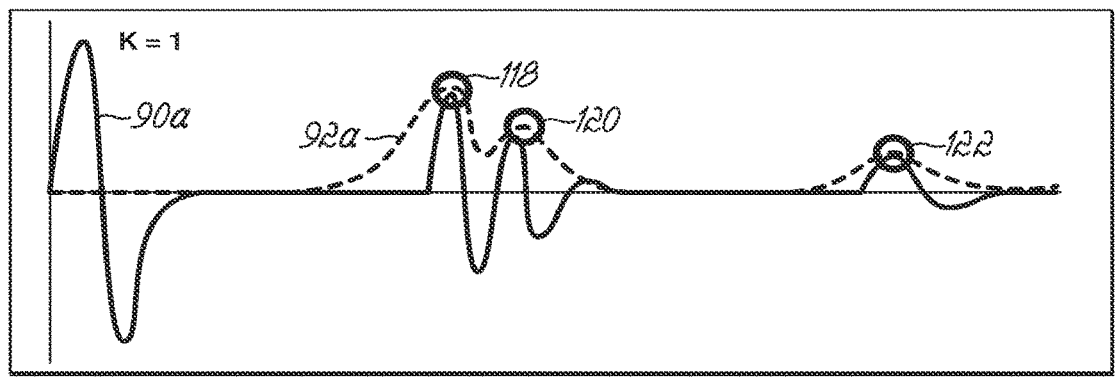
FIGS. 7A-7D are graphical views illustrating an RF signal, a signal envelope generated from the RF signal, and a plurality of amplitude peaks identified in the signal envelope using a non-linear, non-Gaussian filter.
Figure 7B:
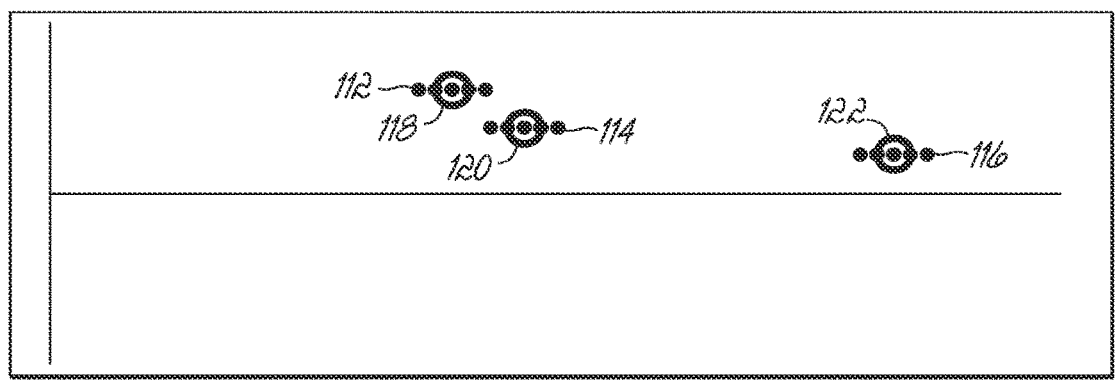

If the second class of filter is to be used, the application 52 proceeds to block 110 rather than block 86 of flow chart 80, and selects a non-linear, non-Gaussian model that follows the recursive Bayesian filter approach. In block 112, the application 52 estimates an optimal time delay using a sequential Monte Carlo method, or particles filter, to identify signal envelope peaks. An example of a particles filter is illustrated in FIGS. 7A and 7B. In principle, the particle filter generates a set of N unweighted particles ($\rho_{k,fk}$) 112, 114, 116 around each envelope peak 118, 120, 122 of the peak data matrix detected during the initialization. The sets of unweighted particles are based an arbitrary statistical density ($\mathbb{P}$), which is approximated by:

$$\rho_{k,fk}^{i:1\to N} \sim \mathbb{P}(p_{k,fk}|s_{obs}) \quad \text{(Equation 7)}$$

These particles 112, 114, 116 predict the peak locations at $f_{k+1}$ via the following equation:

$$p_{est,fk+1}^{i:1\to N}=H(\rho_{k,fk}^{i:1\to N}) \quad \text{(Equation 8)}$$

where H is the estimation function.

Figure 7C:
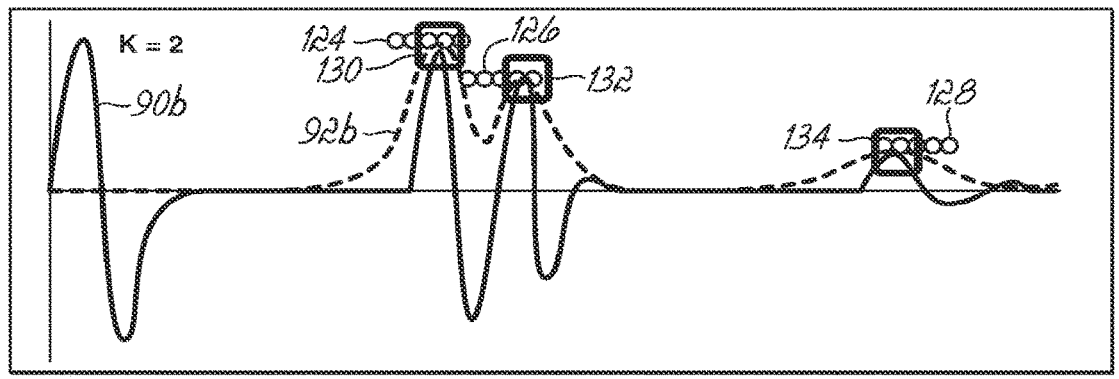
Figure 7D:
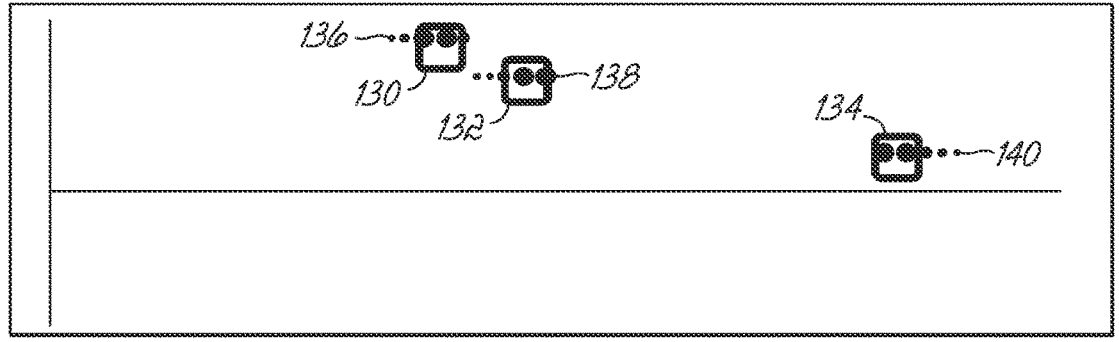

Referring now to FIGS. 7C and 7D, at time k=2, a new peak data matrix ($p_{k,fk}$) is calculated when the RF signal 90b ($s_{obs}$) becomes available, and new sets of estimation particles 124, 126, 128 are made around each peak 130, 132, 134 for ($f_k=f_2$). The estimation particles of sets 112, 114, 116 from time k=1 are compared with the observed data obtained at time k=2, and an error is determined using the following equation:

$$\varepsilon_k^{i:1\to N}=p_{est,fk}^{i:1\to N}-p_{k,fk} \quad \text{(Equation 9)}$$

Figure 8:
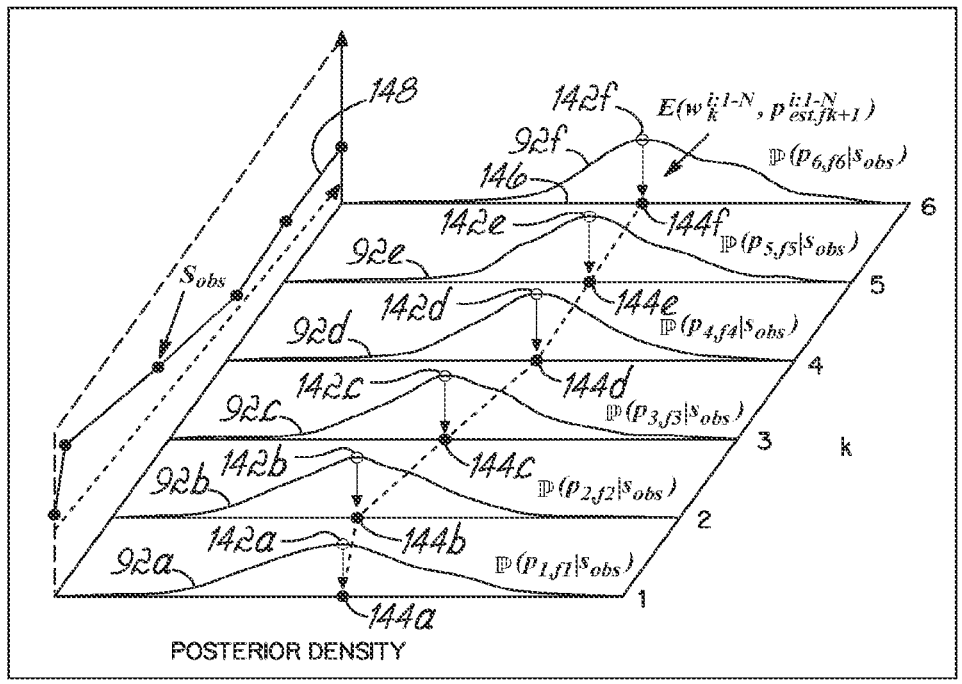
FIG. 8 is a graphical view illustrating one method by which a contour line is derived from a plurality of ultrasound scan line signal envelopes.

The normalized importance weights of the particles of particle sets 124, 126, 128 are evaluated as:

$$w_k^{i:1\to N} = \frac{\varepsilon_k^{i:1\to N}}{\sum_i^N \varepsilon_k^j} \quad \text{(Equation 10)}$$

which produces weighted particle sets 136, 138, 140. This step is generally known as importance sampling where the algorithm approximates the true probabilistic density of the system. An example of importance sampling is shown in FIG. 8, which illustrates a series of signal envelopes 92a-92f for times k=1-6. Each signal envelope 92a-92f includes a peak 142a-142f and a projection 144a-144f of the peak 142a-142f onto a scan-line time scale 146 that indicates the echo return time. These projections 144a-144f may, in turn, be plotted as a contour 148 that represents an estimated location of a tissue density transition or surface. In any case, the expectation of the peak data matrix can then be calculated based on the importance weight and the particles' estimate:

$$p_{k,fk}=\mathbb{E}(w_k^{i:1\to N},p_{est,fk+1}^{i:1\to N}) \quad \text{(Equation 11)}$$

In addition, particle maintenance may be required to avoid particle degeneracy, which refers to a result in which the weight is concentrated on only one particle. Particle re-sampling can be used by replacing degenerated particles with new particles sampled from the posterior density:

$$\mathbb{P}(p_{est,fk+1}^{i:1\to N}) \quad \text{(Equation 12)}$$

Figure 9:
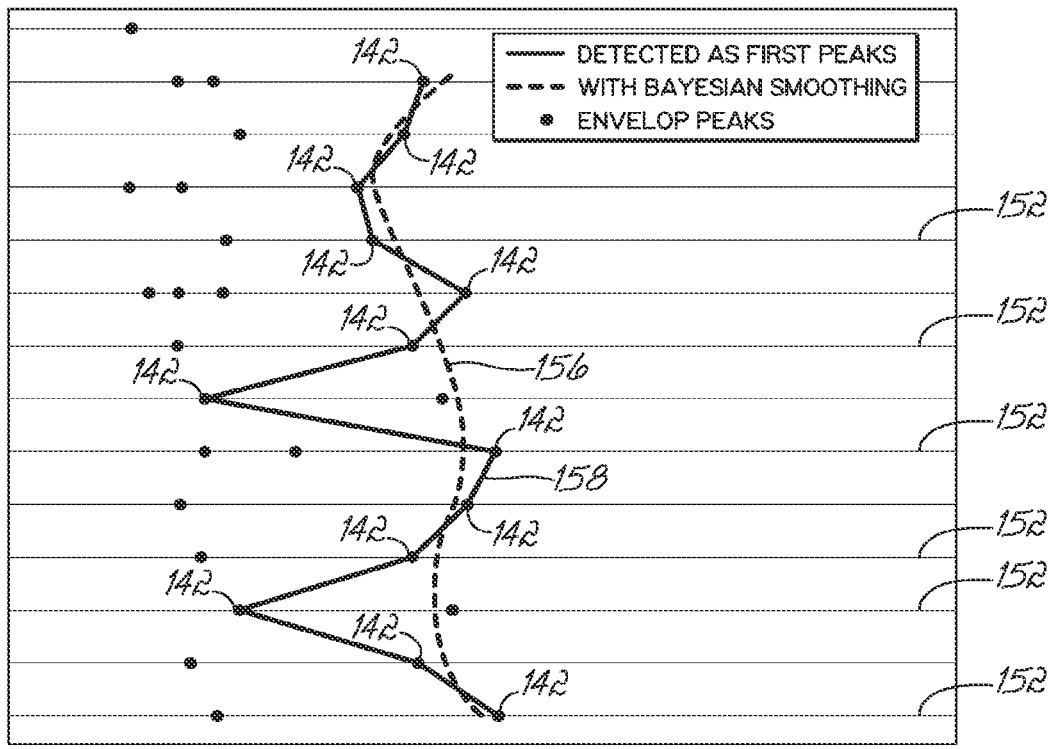
FIG. 9 is a graphical view illustrating a contour generated from a plurality of ultrasound scan line envelopes using first peak detection, and a contour generated from the plurality of scan line envelopes using a Bayesian smoothing filter.

Referring now to FIG. 9, once the envelope peaks have been identified, the application 52 proceeds to block 150 and applies Bayesian smoothing to the envelope peaks 142 in temporally adjacent scan lines 152 before proceeding to block 154 and extracting 2-D features from the resulting smoothed contour line 156. This second layer of the filter thus applies a Bayesian technique to smooth the detected features on a two dimensional level. Conventional peak detection methods have a limitation in that the envelope peaks 142 across different scan lines are not statistically weighted. Thus, only the peaks 142 with the highest power are detected for reconstruction. This may result in an erroneous contour, as illustrated by contour line 158, which connects the envelope peaks 142 having the highest amplitude. Therefore, signal artifacts or improper amplitude compensation by gain control circuits in the RF signal path may obfuscate the signal envelope containing the feature of interest by distorting envelope peak amplitude. Hence, the goal of filtering in the second layer is to correlate signals from different scan lines to form a matrix that determines or identifies two-dimensional features.

This is achieved in embodiments of the invention by Bayesian model smoothing, which produces the smoother exemplary contour line 156. The principle is to examine the signal envelope data retrospectively and attempt to reconstruct the previous state. The primarily difference between the Bayesian estimator and the smoother is that the estimator propagates the states forward in each recursive scan, while the smoother operates in the reverse direction. The initial state of the smoother begins at the last measurement and propagates backward. A common implementation of a smoother is the Rauch-Tung-Striebel (RTS) smoother. The feature embedded in the ultrasound signal is initialized based on a priori knowledge of the scan, which may include ultrasound transducer position data received from the electromagnetic tracking system 26. Sequential features are then estimated and updated in the ultrasound scan line with the RTS smoother.

In an embodiment of the invention, the ultrasound transducer 24 is instrumented with the electromagnetic or optical tracking element 63 so that the motion of the ultrasound transducer 24 is accurately known. This tracking data 160 is provided to the application 52 in block 162, and is needed to determine the position of the ultrasound transducer 24 since the motion of the transducer 24 is arbitrary relative to the patient's joint 12. As scans are acquired by the transducer 24, the system estimates 3-D features of the joint 12, such as the shape of the bone and soft tissue. A tracking problem of this type can be viewed as a probabilistic inference problem in which the objective is to calculate the most likely value of a state vector $X_i$ given a sequence of measurements $y_i$, which are the acquired scans. In an embodiment of the invention, the state vector $X_i$ is the position of the ultrasound transducer 24 with respect to some fixed known coordinate system (such as the ultrasound machine at time k=0), as well as the modes of the bone deformation. Two main steps in tracking are:

(1) Prediction—Given measurements up through time k=i-1, what state can be predicted for time k=i? To do this, the conditional probability $P(X_i|y_0, y_1, \ldots, y_{i-1})$, called the prior distribution, must be computed. If it is assumed that the process is a first order Markov process, this can be computed by integrating $P(X_i|X_{i-1})P(X_i|y_0, y_1, \ldots, y_{i-1})$ over all $X_{i-1}$.

and (2) Correction—Given a new measurement $y_i$, correct the estimate of the state. To do this, the probability $P(X_i|y_0, y_1, \ldots, y_i)$, called the posterior distribution, must be computed.

A system dynamics model relates the previous state $X_{i-1}$ to the new state $X_i$ via the transitional distribution $P(X_i|X_{i-1})$, which is a model of how the state is expected to evolve with time. In an embodiment of the invention, $X_i$ are the 3-D feature estimates calculated from the Bayesian contour estimation performed during tier 2 filtering, and the transformation information contains the translations and rotations of the data obtained from the tracking system 26. With joint imaging, the optimal density or features are not expected to change over time, because the position of the bone is fixed in space and the shape of the bone scanned does not change. Hence, the transitional distribution does not alter the model states.

A measurement model relates the state to a predicted measurement, y=f(X). Since there is uncertainty in the measurement, this relationship is generally expressed in terms of the conditional probability $P(y_i|X_i)$, also called the likelihood function. In an embodiment of the invention, the RF signal and a priori feature position and shape are related by an Anisotropic Iterative Closest Point (AICP) method.

To estimate position and shape of the feature, the application 52 proceeds to block 164. At block 164, the application 52 performs an AICP method that searches for the closest point between the two datasets iteratively to establish a correspondence by the anisotropic weighted distance that is calculated from the local error covariance of both datasets. The correspondence is then used to calculate a rigid transformation that is determined iteratively by minimizing the error until convergence. The 3-D features can then be predicted based on the received RF signal and the a priori feature position and shape. By calculating the residual error between the predicted 3-D feature and the RF signal data, the a priori position and shape of the feature are updated and corrected in each recursion. Using Bayes' rule, the posterior distribution can be computed based on measurements from the raw RF signal.

If both the dynamic model and the measurement model are linear with additive Gaussian noise, then the conditional probability distributions are normal distributions. In particular, $P(X_i|y_0, y_1, \ldots, y_i)$ is unimodal and Gaussian, and thus can be represented using the mean and covariance of the predicted measurements. Unfortunately, the measurement model is not linear and the likelihood function $P(y_i|X_i)$ is not Gaussian. One way to deal with this is to linearize the model about the local estimate, and assume that the distributions are locally Gaussian.

Figure 10:
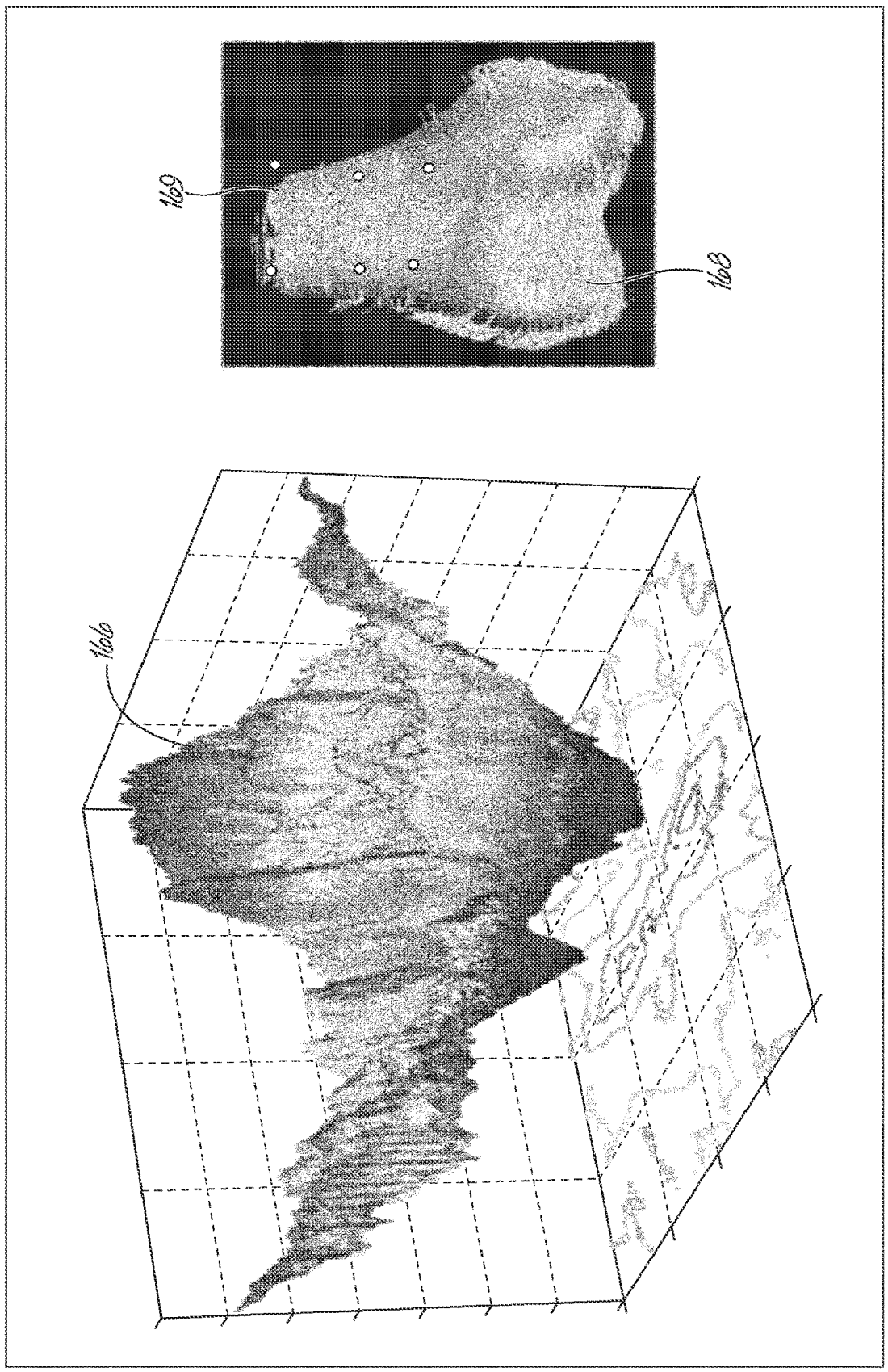
FIG. 10 is a 3-D view of an ultrasound frame after envelope detection, and a corresponding registered point cloud for an imaged joint.

Referring to FIG. 10, a surface 166 representing an exemplary probability distribution associated with a point cloud 168 of a scanned bone 169 illustrates that the probability distribution for the measurement model is not Gaussian, and has many peaks. This suggests multiple hidden states are presented in the model. The posterior probability $P(X_i|y_0, y_1, \ldots, y_i)$ would also have multiple peaks. The problem would be worse if the state included shape parameters as well as position. A linear tracking filter such as the Kalman filter (or its nonlinear extension, the Extended Kalman filter) cannot deal with non-linear and non-Gaussian system with multi-peaks distribution, which may converge upon the wrong solution.

Instead of treating the probability distributions as Gaussian, a statistical inference can be performed using a Monte Carlo sampling of the states. The optimal position and shape of the feature are thereby estimated through the posterior density, which is determined from sequential data obtained from the RF signals. For recursive Bayesian estimation, this approach, known as particle filtering, has been found to be useful in dealing in applications where the state vector is complex and the data contain a great deal of clutter, such as tracking objects in image sequences. The basic idea is to represent the posterior probability by a set of independent and identically distributed weighted samplings of the states, or particles. Given enough samples, even very complex probability distributions can be represented. As measurements are taken, the importance weights of the particles are adjusted using the likelihood model, using the equation $w_j' = P(y_i|X_i) w_j$, where $w_j$ is the weight of the jth particle. This is known as importance sampling.

The principal advantage of this method is that the method can approximate the true probability distribution of the system, which cannot be determined directly, by approximating a finite set of particles from a distribution from which samples can be drawn. As measurements are obtained, the algorithm adjusts the particle weights to minimize the error between the prediction and observation states. With enough particles and iterations, the posterior distribution will approach the true density of the system. A plurality of bone or other anatomical feature surface contour lines is thereby generated that can be used to generate 3-D images and models of the joint or anatomical feature. These models, in turn, may be used to facilitate medical procedures, such as joint injections, by allowing the joint or other anatomical feature to be visualized in real time during the procedure using an ultrasound scan.

Figure 11:
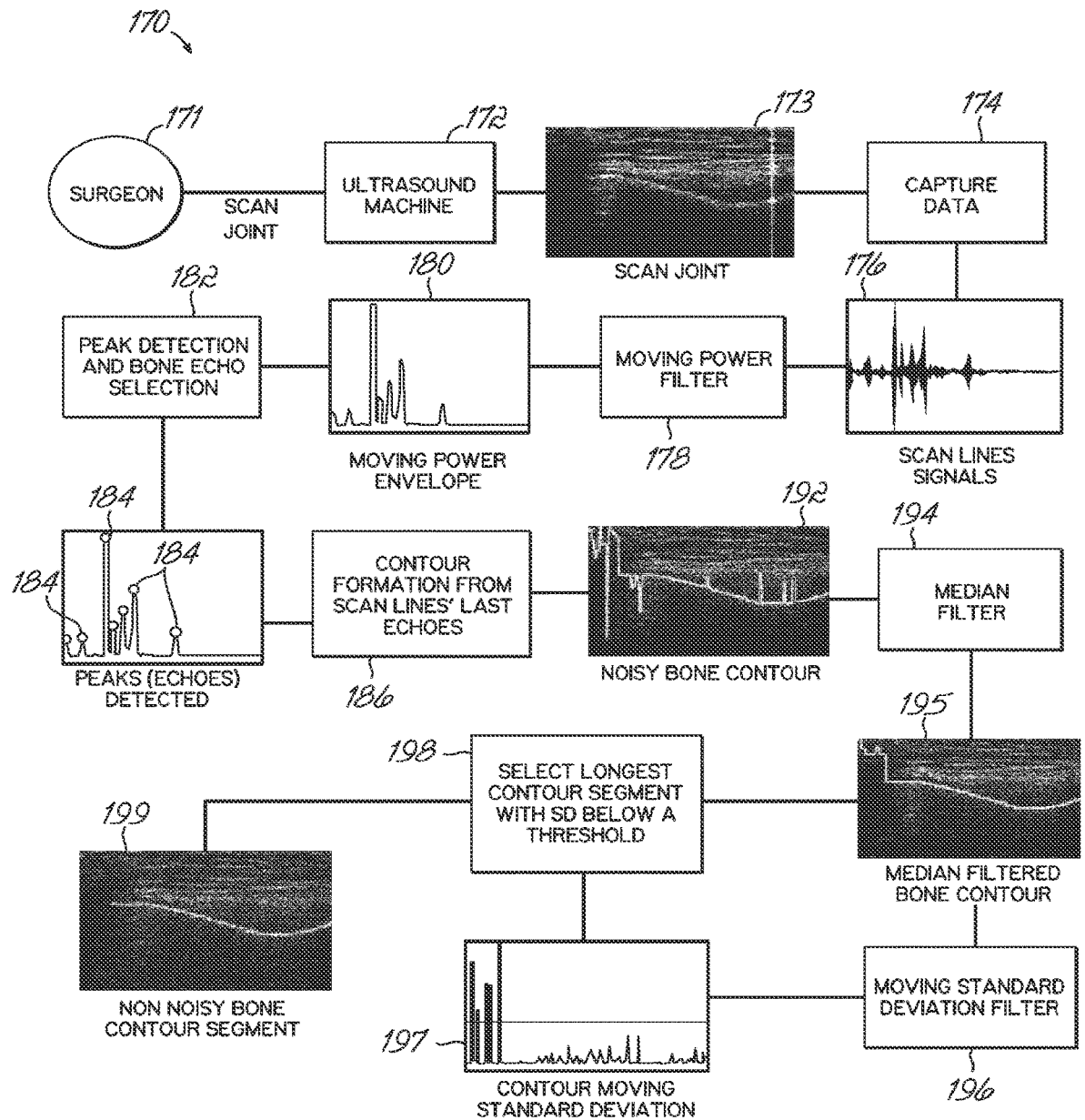
FIG. 11 is a flow chart illustrating an alternative method by which the imaging system in FIG. 3 generates a real-time 3-D image.
Figure 12:
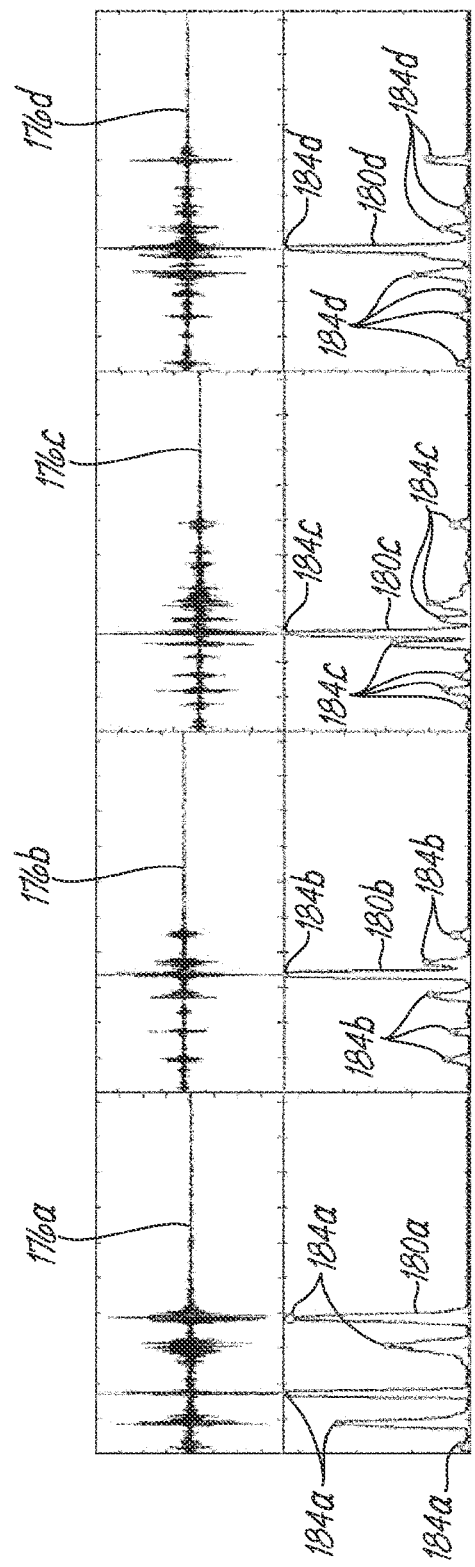
FIG. 12 is a graphical view illustrating a sequence of ultrasound scan lines and their corresponding signal envelopes.

Referring now to FIG. 11, a flow chart 170 illustrates a process for generating a 3-D joint model in accordance with another embodiment of the invention in which a bone contour is generated from raw ultrasound RF signal data. This contour detection includes detecting the echoes within the raw RF signals. To this end, in blocks 171-174, a surgeon 171 or treating physician uses an ultrasound machine 172 to scan the joint 173 being modeled. RF data is captured 174 to produce scan line RF signals 176. These RF signals 176 represent the return echoes from a plurality of ultrasound scans. The RF signals 176 are processed by a moving power filter 178 to generate a moving power envelope 180. This process is illustrated in more detail in FIG. 12, which shows a series of scan line RF signals 176a-176d obtained as the transducer 24 is moved over the joint 12. Each scan line RF signal 176a-176d is processed by the application 52 to produce a corresponding moving power envelope 180a-180d. In block 182 of flow chart 170, peaks 184 are identified in the power envelope 180. These peaks 184 may represent an abrupt change in tissue density, such as that associated with a bone or cartilage surface. As shown in FIG. 12, the positions of the peaks 184a-184d shift as the transducer 24 is moved, indicating the distance between the transducer 24 and the tissue density transitions reflecting the transmitted ultrasound signals 62 has changed.

Figure 13:
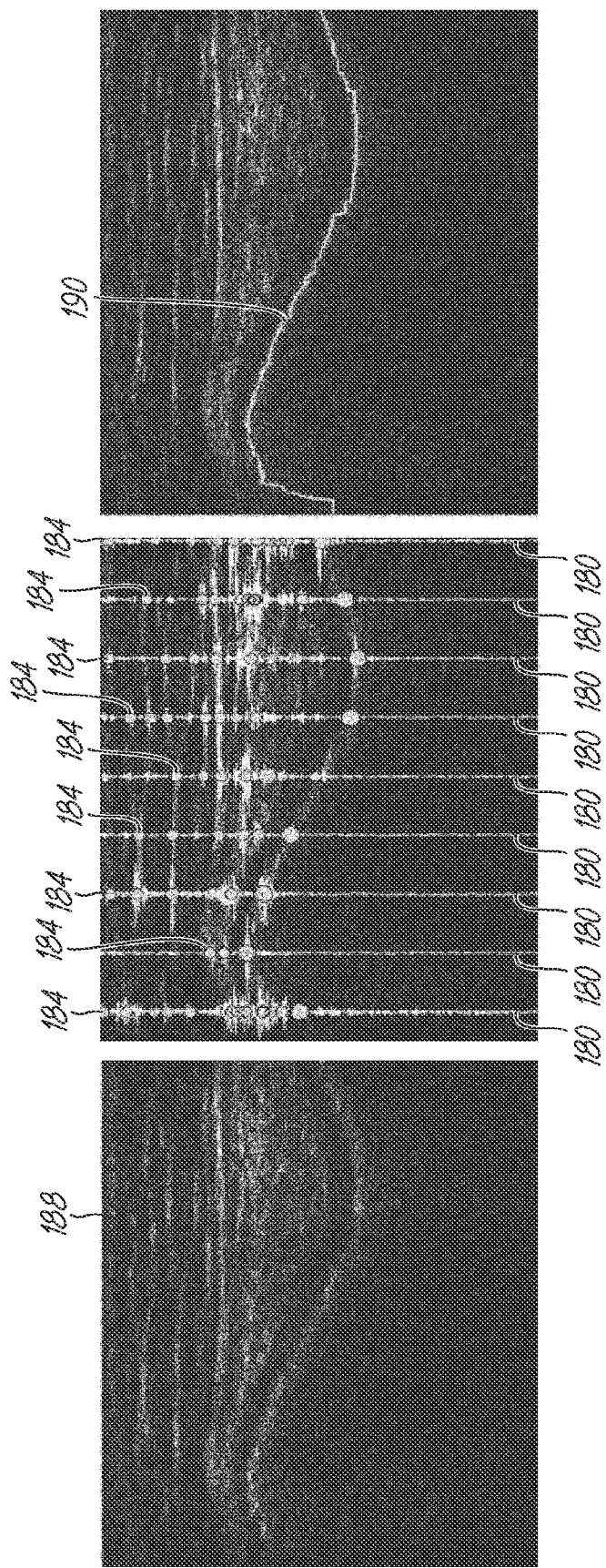
FIGS. 13A-13C are 2-D views illustrating a sequence of ultrasound scan lines, signal envelopes, and an associated contour line.
Figure 14:
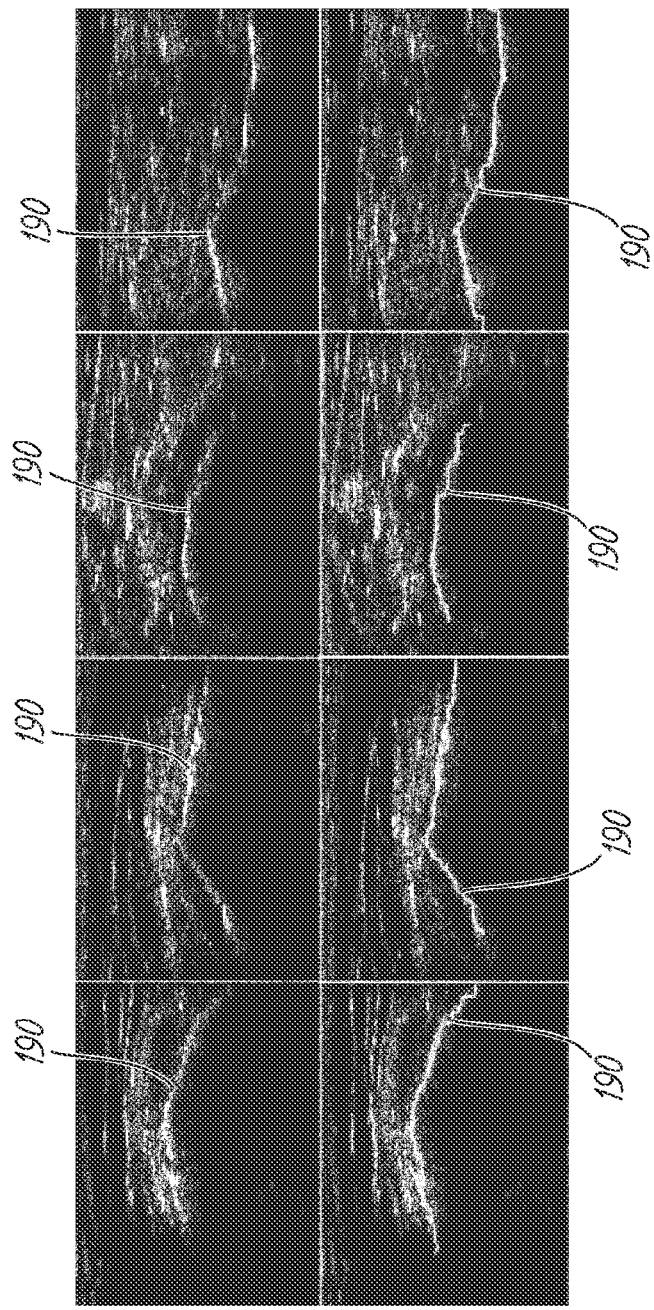
FIG. 14 is a view of a series of ultrasound frames, with each frame showing a contour line.

In block 186, and as shown in more detail in FIGS. 13A-13C, a bone contour is generated from the last echo or peak 184 detected in the scan line. This process of generating the bone contour begins with a 2-D diagnostic ultrasound presentation of echo-producing interfaces in a single plane, also known as a brightness or B-mode image 188, as shown in FIG. 13A. FIG. 13B illustrates a plurality of power envelopes 180 with identified peaks 184 as seen from above. The last or bottom peak 184 in each power envelope 180 is identified and connected with a line 190 that represents the bone contour, as shown in FIG. 13C. The last peak 184 is generally associated with a reflection from a bone surface since ultrasound signals 62 typically will not penetrate bone. A sequence of multiple bone contours 190 may be generated as the ultrasound transducer 24 is moved about the joint 12, examples of which are illustrated in FIG. 14.

In some cases, the raw scan line RF signals 176 may contain noise sufficient to produce false peaks 184. This may in turn produce a noisy bone contour 192. The noisy contour 192 may be filtered in block 194 using a median filter to produce a median filtered bone contour 195. This filtered bone contour 195 is provided to a moving standard deviation filter in block 196, which generates a contour representing the moving standard deviation of the filtered bone contour 197. In block 198, the filtered bone contour 190 is compared to the moving standard deviation contour 197, and the contour having longest segment with a standard deviation below a threshold is selected to produce a non-noisy bone contour segment 199. The resulting bone contour 199 is selected from those segments of the extracted bone contour that satisfy two conditions: (1) the continuity criteria, having a local standard deviation value below selected standard deviation threshold, and (2) a minimum-length criteria, which avoids piecewise-smooth noise contour segments from being falsely detected as bone contour. In some exemplary embodiments, the length of the standard deviation filter may be set to 3 and the threshold set to 1.16 mm, which may correspond to 30 signal samples.

Figure 15:
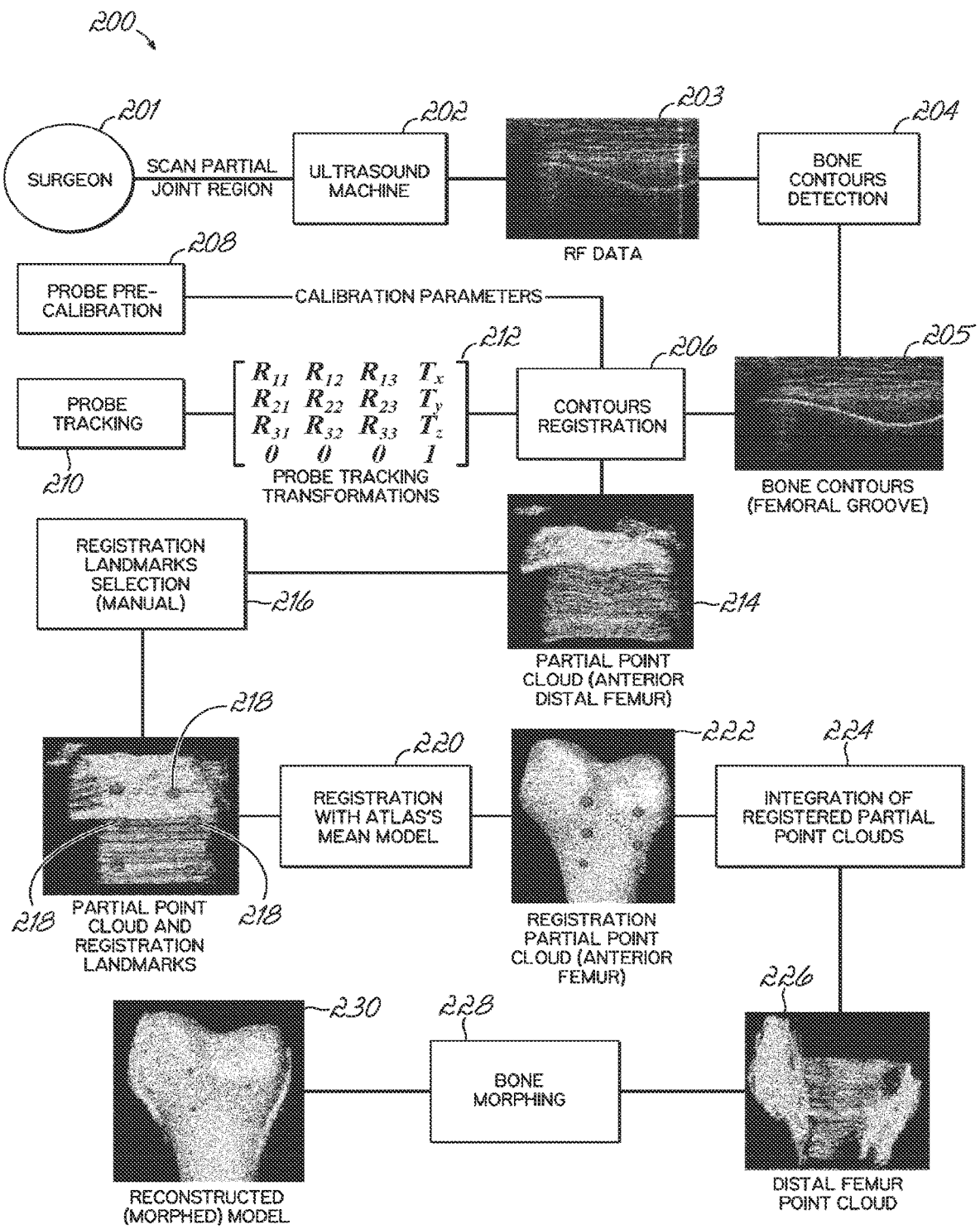
FIG. 15 is a flow chart illustrating a method of generating a 3-D model of a joint using ultrasound and tacking position data.

Referring now to FIG. 15, a flow chart 200 illustrating a process for generating a point cloud and 3-D model reconstruction is presented. In blocks 201-204, the surgeon or treating physician 201 obtains a plurality of bone contours 205 as described above with respect to one of FIG. 4 or 11. In block 206, the position of the probe or ultrasound transducer 24 is registered during acquisition of each bone contour 205. This registration relies on position data determined using position calibration data 208 and probe tracking data 210 processed through a probe tracking matrix or transformation 212. In an embodiment of the invention, the position data may be determined by the electromagnetic tracking system 26 as the contour is being acquired. Based on the registered bone contours that are now defined 205, a partial point cloud 214 of a bone, such as an anterior distal femur, is generated.

In block 216, the physician selects registered landmarks 218 in the partial point cloud 214, which is shown in more detail in FIG. 16A. Once the registered landmarks 218 have been selected, the application 52 proceeds to block 220. In block 220, the landmarks 218 are registered with a bone model selected from a plurality of bone models in an atlas of mean models to produce a registered partial point cloud 222. The plurality of partial point clouds 214 are initially aligned to a standardized or base model 223 of the scanned bone, shown in here as a femur, using the previously specified landmarks 218. This process is illustrated in FIGS. 16B and 16C, and may include reconstructing the bone by morphing the base model 223. The base model 223 may be a mean model or a model selected based on patient demographics from the statistical bone atlas to match the partial point cloud 214. The statistical bone atlas may include data representing the morphology of the bone's anatomy and its inter-subject variation that is based on empirical data collected from a large sample of human subjects. This process may be repeated to generate a plurality of partial point clouds 214.

In block 224, the registered partial point clouds 222 are integrated to generate a distal femur point cloud 226, which is illustrated in more detail in FIG. 16D. In block 228, this point cloud 226 is processed by bone morphing to generate a reconstructed, or morphed, bone model 230, as shown in FIG. 16E.

Figure 17:
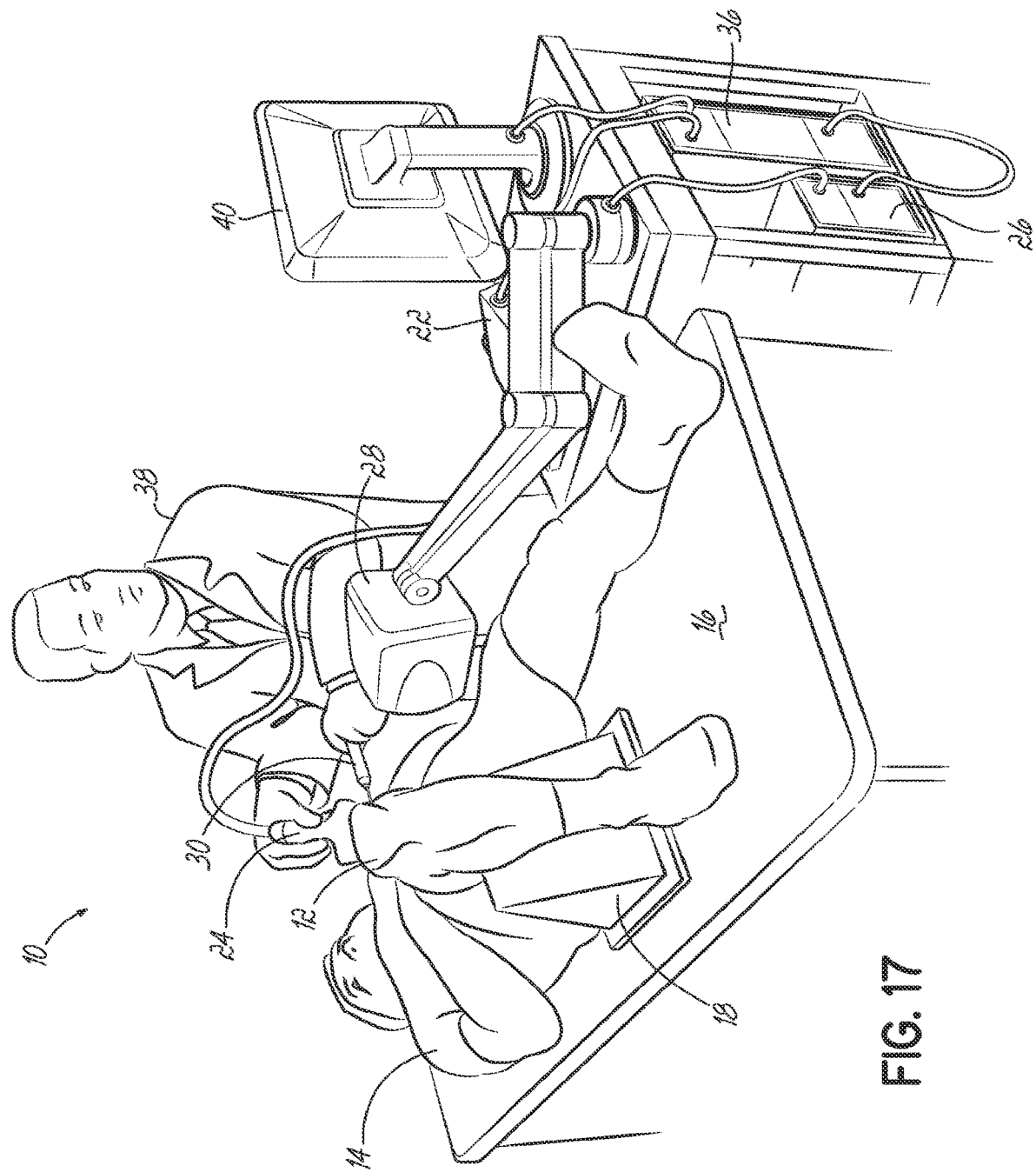
FIG. 17 is a perspective view of the injection suite illustrating an injection procedure.
Figure 18C:
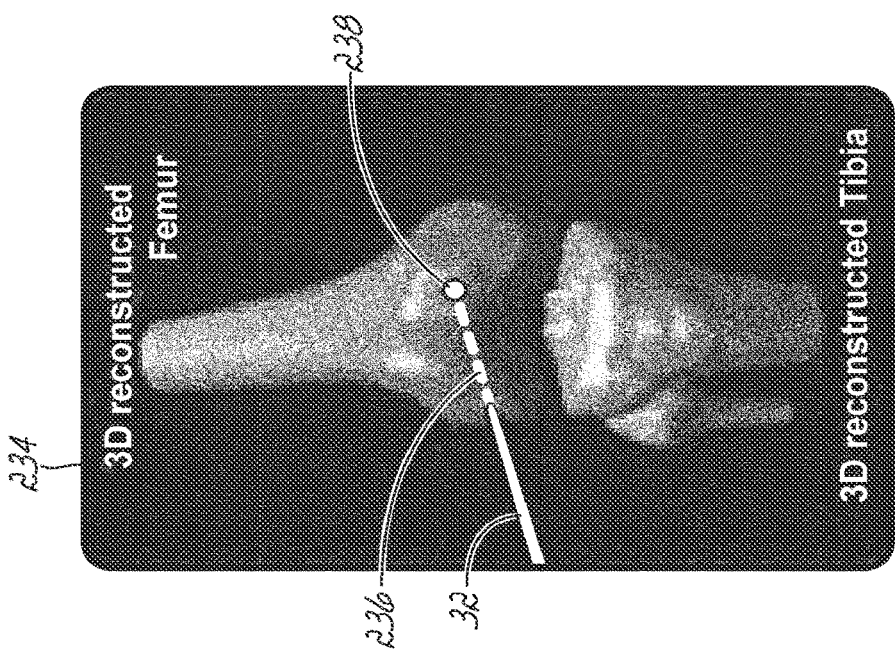
FIGS. 18A-18C are diagrammatic views of the injection procedure of FIG. 17 that include real-time 3-D models to help visually guide an injection needle.
Figure 18B:
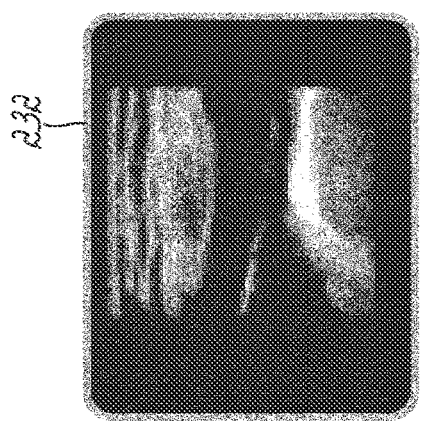
Figure 18A:
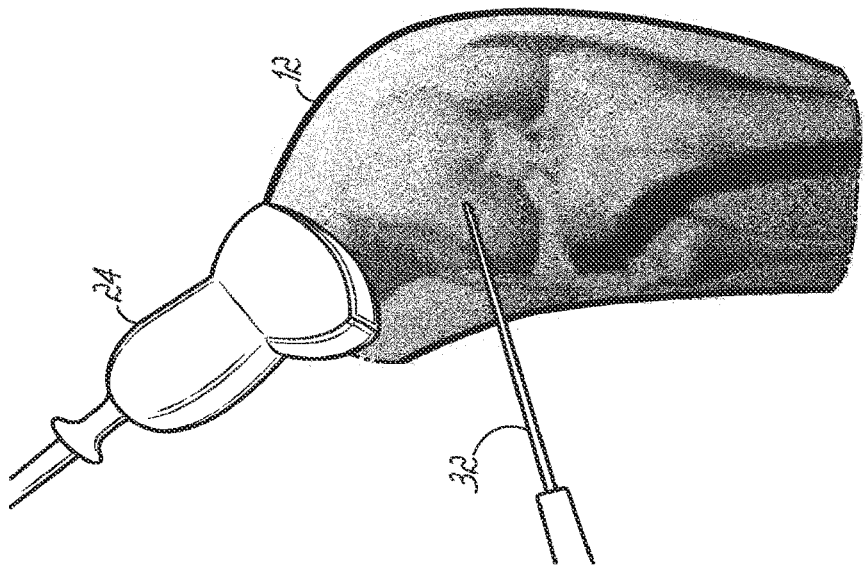
Figure 19:
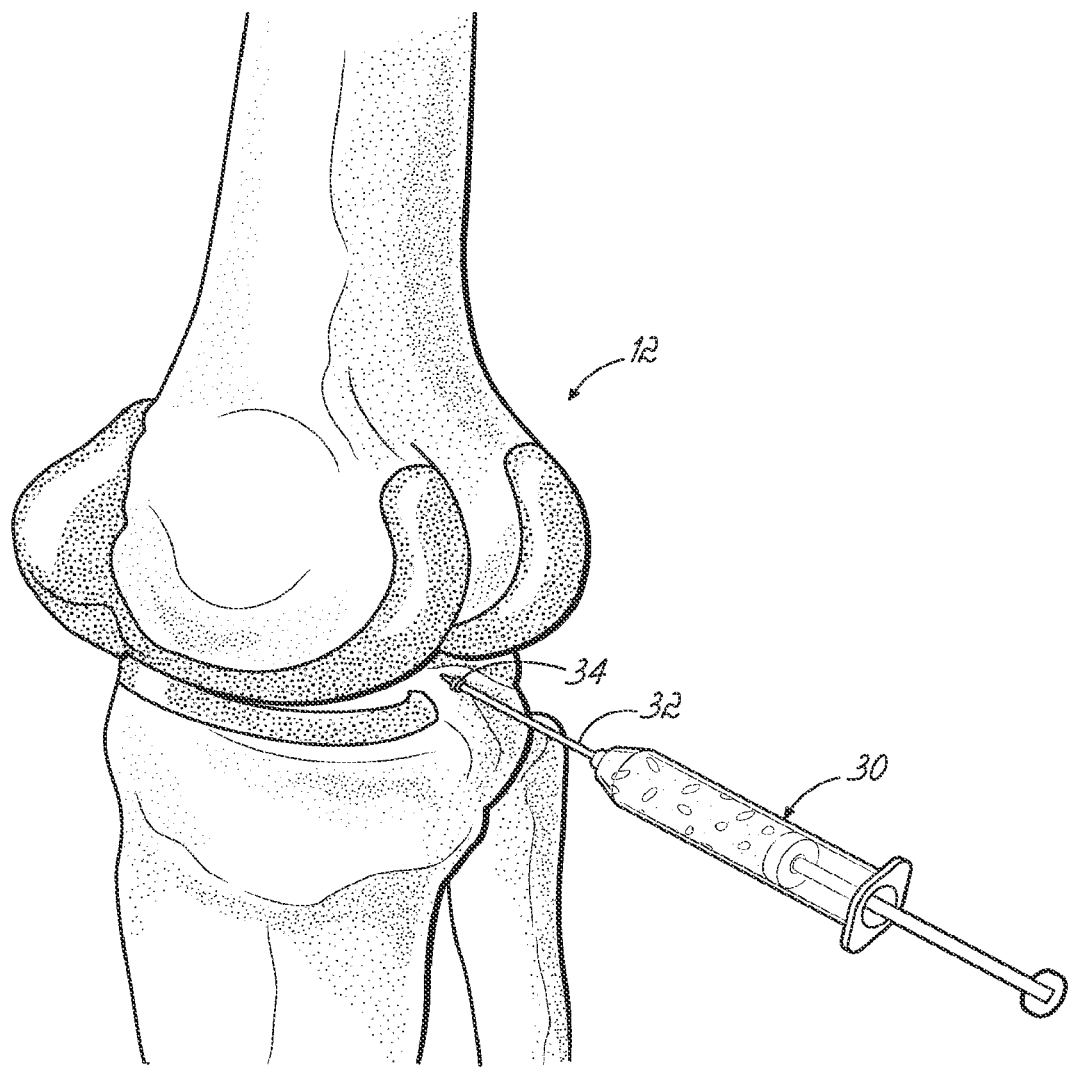
FIG. 19 is a diagrammatic view of a knee joint receiving an injection.

Once the models are complete, the injection may proceed as shown in FIGS. 17-19. For the injection treatment, the patient may be placed supine on the exam table 16 in preparation for injection as shown in FIG. 17, with or without the first positioner 18. The injection needle 32 is outfitted with the electromagnetic tracking element 34 at an assigned location so that the needle tip position relative to the tracking element 34 is known and fixed. The electromagnetic transceiver unit 28 should be placed approximately 20-25 cm distance from the injection site. The ultrasound transducer 24 is used to monitor the joint 12 during injection. There are three commonly used knee injection sites:

anterolateral, anteromedial and lateral midpatellar. Some clinicians may also use a superior lateral injection site at the superior pole of the patella to avoid osteophytes or joint space narrowing at the lateral midpatellar site. The ultrasound transducer 24 should be away from the injection site yet close enough to view the intended injection space within the joint 12, as best shown in FIG. 18A. The 2-D B-mode ultrasound images 232 (FIG. 18B) are shown in real-time with the 3-D models 234 (FIG. 18C) of the femur and tibia registered and provided for visualization on the display 40. As the needle 32 enters the body and approaches the joint space, the 3-D position of the needle 32 is displayed on the monitor 40 screen along with the 3-D model of the patient's knee 12. This allows the physician 38 to view and adjust placement of the final injection location, as best shown in FIG. 18C.

To this end, a path projection 236 may be determined and displayed by the imaging application 52 to indicate a path from the tip of the needle 32 to a desired injection point 238 in the joint 12. This path projection 236 may be displayed as, for example, a red dotted line extending from the needle 32 to the injection point 238. The path projection 236 may be shown on the monitor 40 in response to detecting contact between the needle 32 and the skin of the patient 14. The path projection 236 may help the physician 38 visualize how to guide the needle 32, and may be calculated and recalculated in real-time with every detected motion of the needle 32. That is, the path projection 236 may be continually updated by the imaging application 52. In response to determining that a clear path exists between the needle 32 and the injection point 238, the imaging application 52 may change the appearance of the path projection 236. For example, the application 52 may change the color of the displayed line from red to green to indicate to the physician 38 that the needle 32 has a clear path to the injection point 238.

A sterile holed drape made of Willowwood™ silicon based material and with a dense population of individual A-Mode sensors and IMU, such as described in International Application No. PCT/US2012/050590 entitled 3-D ULTRASOUND IMAGING DEVICE AND METHODS, filed on 13 Aug. 2012, can also be utilized to track joint position and correct for motion during the injection process. The prospective injection site is first sterilized in the normal fashion with betadine and then alcohol. The hole in this sensor drape is placed over the sterilized area for needle entrance, providing sterile access to the joint. The surrounding sensor drape registers the bones and joint so that any motion during injection is adjusted for and does not require re-registration or re-sterilization.

Non-invasive 3-D real-time imaging and needle guidance addresses the clinical need for improved precision and accuracy in joint injections. Additionally, this form or needle guidance has the potential of de-skilling the procedure, potentially changing the site of care from the radiology suite or orthopedic specialist to, for example, a primary care provider. The various embodiments of the present invention, as provided herein, provide an office-based method that replaces fluoroscopy, requires no radiation, and increases the injection efficacy of stem cells and/or platelet rich plasma ("PRP") therapy.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A method of generating a 3D patient-specific bone model, the method comprising:
    acquiring a plurality of raw signals from an ultrasound scan of a patient's bone using an ultrasound probe;
    tracking the acquiring of the raw signals in three dimensional ("3D") space and generating corresponding tracking data;
    transforming each raw signal into an envelope comprising a plurality of peaks by applying an envelope detection algorithm to each signal, each peak corresponding with a tissue interface echo;
    identifying a bone echo from the tissue interface echoes of each raw signal;
    determining a two dimensional ("2D") bone contour from the plurality of bone echoes corresponding to each scan location of the ultrasound probe, thereby resulting in 2D bone contours;
    transforming the 2D bone contours into an integrated 3D point cloud using the tracking data; and
    deforming a non-patient specific 3D bone model corresponding to the patient's bone in correspondence with the integrated 3D point cloud to generate a 3D patient-specific bone model.

2. The method of claim 1, wherein applying an envelope detection algorithm to each signal comprises applying a moving power filter to each raw signal.

3. The method of claim 1, wherein tracking the acquisition includes using at least one of an optical position tracking system and an electromagnetic position tracking system.

4. The method of claim 1, wherein the non-patient specific 3D bone model is utilized to filter noise by thresholding for a distance between a respective point of the integrated 3D point cloud and the non-patient specific 3D bone model.

5. The method of claim 1, further comprising identifying the 2D bone contour by removing portions of the bone echo that deviate from a continuous portion of the bone echo.

6. The method of claim 1, wherein the non-patient specific 3D bone model is an average bone model of a plurality of bone models in a statistical atlas.

7. The method of claim 1, wherein transforming the 2D bone contours into an integrated 3D point cloud further comprises:
    transforming the 2D bone contours into a plurality of registered 3D partial point clouds; and,
    integrating the plurality of registered 3D partial point clouds to form the integrated 3D point cloud.

8. The method of claim 1, wherein deforming the non-patient specific 3D bone model comprises comparing the non-patient specific 3D bone model with the 3D point cloud and, based on the comparing, deforming the non-patient specific 3D bone model to match the 3D point cloud.

9. The method of claim 8, wherein the comparing and deforming are iteratively performed until the comparing results in a deviation that is less than a deviation threshold.

10. The method of claim 1, wherein the 3D patient-specific bone model includes at least one of a 3D patient-specific model of a bone, a 3D patient-specific model of a joint, and a 3D patient-specific model of cartilage.

11. The method of claim 1, wherein the ultrasound scan comprises an A-mode ultrasound scan.

12. The method of claim 1, wherein the ultrasound scan occurs over a plurality of locations the patient's bone.

13. The method of claim 1, wherein identifying the bone echo includes selecting a last peak having a normalized envelope amplitude above a preset threshold.

14. The method of claim 13, wherein the envelope amplitude is normalized with respect to a maximum peak existing in the envelope.

15. A method of generating a 3D patient-specific bone model, the method comprising:
- acquiring a plurality of signals from an ultrasound scan of a patient's bone and generating tracking data in three dimensional ("3D") space corresponding to acquisition of the plurality of signals;
- transforming each of the plurality of signals into an envelope comprising a plurality of peaks, each peak corresponding with a tissue interface echo;
- identifying bone echoes from tissue interface echoes;
- determining a plurality of two dimensional ("2D") bone contours from the bone echoes;
- transforming the 2D bone contours into a 3D point cloud using the tracking data; and,
- deforming a non-patient specific 3D bone model using the 3D point cloud to generate a 3D patient-specific bone model.

16. The method of claim 15, further comprising identifying the bone contours by removing portions of the bone echoes that deviate from a continuous portion of the bone echoes.

17. The method of claim 15, wherein the non-patient specific 3D bone model is an average bone model of a plurality of bone models in a statistical atlas.

18. The method of claim 15, wherein transforming the 2D bone contours into a 3D point cloud further comprises:
- transforming the 2D bone contours into a plurality of registered 3D partial point clouds; and,
- integrating the plurality of registered 3D partial point clouds to form the integrated 3D point cloud.

19. The method of claim 15, wherein deforming the non-patient specific 3D bone model comprises comparing the non-patient specific 3D bone model with the 3D point cloud and, based on the comparing, deforming the non-patient specific 3D bone model to match the 3D point cloud.

20. The method of claim 15, wherein identifying the bone echoes includes selecting peaks having a normalized envelope amplitude above a preset threshold.

* * * * *